US006777596B1

(12) United States Patent
Carrigan

(10) Patent No.: US 6,777,596 B1
(45) Date of Patent: Aug. 17, 2004

(54) HYBRID MAIZE PLANT & SEED 38A24

(75) Inventor: Lori L. Carrigan, Spicer, MN (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 09/489,223

(22) Filed: Jan. 21, 2000

(51) Int. Cl.[7] .............................. A01H 5/10; A01H 5/00; A01H 1/00; A01H 1/04; C12N 5/04

(52) U.S. Cl. .................. 800/320.1; 435/412; 435/430.1; 800/260; 800/274; 800/275; 800/284; 800/300.1; 800/302; 800/303

(58) Field of Search .............................. 800/284, 320.1, 800/298, 300.1, 301, 302, 303, 260, 271, 274, 275, 278; 435/410, 412, 424, 430.1

(56) References Cited

U.S. PATENT DOCUMENTS

| | | | |
|---|---|---|---|
| 4,812,599 A | | 3/1989 | Segebart |
| 5,574,208 A | * | 11/1996 | Luedtke, Jr. ................. 800/200 |
| 6,180,857 B1 | * | 1/2001 | Carlone, Jr. ............. 800/320.1 |

OTHER PUBLICATIONS

Conger, B.V., et al. (1987) "Somatic Embryogenesis From Cultured Leaf Segments of Zea mays", Plant Cell Reports, 6:345–347.

Duncan, D.R., et al. (1985) "The Production of Callus Capable of Plant Regeneration From Immature Embryos of Numerous Zea mays Genotypes", Planta, 165:322–332.

Edallo, et al. (1981) "Chromosomal Variation and Frequency of Spontaneous Mutation Associated with in Vitro Culture and Plant Regeneration in Maize", Maydica, XXVI:39–56.

Green, et al. (1975) "Plant Regeneration From Tissue Cultures of Maize", Crop Science, vol. 15, pp. 417–421.

Green, C.E., et al. (1982) "Plant Regeneration in Tissue Cultures of Maize" Maize for Biological Research, pp. 367–372.

Hallauer, A.R. et al. (1988) "Corn Breeding" Corn and Corn Improvement, No. 18, pp. 463–481.

Meghji, M.R., et al. (1984) "Inbreeding Depression, Inbred & Hybrid Grain Yields, and Other Traits of Maize Genotypes Representing Three Eras", Crop Science, vol. 24, pp. 545–549.

Phillips, et al. (1988) "Cell/Tissue Culture and In Vitro Manipulation", Corn & Corn Improvement, 3rd Ed., ASA Publication, No. 18, pp. 345–387.

Poehlman et al (1995) Breeding Field Crop, 4th Ed., Iowa State University Press, Ames, IA., pp. 132–155 and 321–344.

Rao, K.V., et al., (1986) "Somatic Embryogenesis in Glume Callus Cultures", Maize Genetics Cooperative Newsletter, No. 60, pp. 64–65.

Sass, John F. (1977) "Morphology", Corn & Corn Improvement, ASA Publication, Madison, WI pp. 89–109.

Songstad, D.D. et al. (1988) "Effect of ACC(1–aminocyclopropane–1–carboyclic acid), Silver Nitrate & Norbonadiene on Plant Regeneration From Maize Callus Cultures", Plant Cell Reports, 7:262–265.

Tomes, et al. (1985) "The Effect of Parental Genotype on Initiation of Embryogenic Callus From Elite Maize (Zea mays L.) Germplasm", Theor. Appl. Genet., vol. 70, p. 505–509.

Troyer, et al. (1985) "Selection for Early Flowering in Corn: 10 Late Synthetics", Crop Science, vol. 25, pp. 695–697.

Umbeck, et al. (1983) "Reversion of Male–Sterile T–Cytoplasm Maize to Male Fertility in Tissue Culture", Crop Science, vol. 23, pp. 584–588.

Wright, Harold (1980) "Commercial Hybrid Seed Production", Hybridization of Crop Plants, Ch. 8:161–176.

Wych, Robert D. (1988) "Production of Hybrid Seed", Corn and Corn Improvement, Ch. 9, pp. 565–607.

* cited by examiner

Primary Examiner—Ashwin Mehta
(74) Attorney, Agent, or Firm—McKee, Voorhees & Sease, P.L.C.

(57) ABSTRACT

According to the invention, there is provided a hybrid maize plant, designated as 38A24, produced by crossing two Pioneer Hi-Bred International, Inc. proprietary inbred maize lines. This invention relates to the hybrid seed 38A24, the hybrid plant produced from the seed, and variants, mutants, and trivial modifications of hybrid 38A24. This invention also relates to methods for producing a maize plant containing in its genetic material one or more transgenes and to the transgenic maize plants produced by that method. This invention further relates to methods for producing maize lines derived from hybrid maize line 38A24 and to the maize lines derived by the use of those methods.

18 Claims, No Drawings

HYBRID MAIZE PLANT & SEED 38A24

FIELD OF THE INVENTION

This invention is in the field of maize breeding, specifically relating to hybrid maize designated 38A24.

BACKGROUND OF THE INVENTION

Plant Breeding

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Maize (*Zea mays* L.), often referred to as corn in the United States, can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

The development of a hybrid maize variety in a maize plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with unrelated inbred lines to produce the hybrid progeny (F1). During the inbreeding process in maize, the vigor of the lines decreases. Vigor is restored when two different inbred lines are crossed to produce the hybrid progeny (F1). An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid corn plants can then be generated from this hybrid seed supply.

Large scale commercial maize hybrid production, as it is practiced today, requires the use of some form of male sterility system which controls or inactivates male fertility. A reliable method of controlling male fertility in plants also offers the opportunity for improved plant breeding. This is especially true for development of maize hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid maize seed is typically produced by a male sterility system incorporating manual or mechanical detasseling. Alternate strips of two inbred varieties of maize are planted in a field, and the pollenbearing tassels are removed from one of the inbreds (female) prior to pollen shed. Providing that there is sufficient isolation from sources of foreign maize pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled fertile maize and CMS produced seed of the same hybrid are blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. No. 3,861,709 and 3,710,511. These and all patents referred to are incorporated by reference. In addition to these methods, Albertsen et al., of Pioneer Hi-Bred, U.S. patent application Ser. No. 5,432,068, have developed a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 8913010153.8 publication no. 329, 308 and PCT application PCT/CA90/00037 published as WO 90/08828).

Another system useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. : 4,936,904). Application of the gametocide, timing of the application and genotype specificity often limit the usefulness of the approach.

The use of male sterile inbreds is but one factor in the production of maize hybrids. The development of maize hybrids in a maize plant breeding program requires, in general, the development of homozygous inbred lines, the crossing of these lines, and the evaluation of the crosses.

Maize plant breeding programs combine the genetic backgrounds from two or more inbred lines or various other broad-based sources into breeding pools from which new inbred lines are developed by selfing and selection of desired phenotypes. Hybrids also can be used as a source of plant breeding material or as source populations from which to develop or derive new maize lines. Plant breeding techniques known in the art and used in a maize plant breeding program include, but are not limited to, recurrent selection backcrossing, pedigree breeding, restriction length polymorphism enhanced selection, genetic marker enhanced selection and transformation. The inbred lines derived from hybrids can be developed using said methods of breeding such as pedigree breeding and recurrent selection. New inbreds are crossed with other inbred lines and the hybrids from these crosses are evaluated to determine which of those have commercial potential.

Recurrent selection breeding, backcrossing for example, can be used to improve inbred lines and a hybrid which is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait and for the germplasm inherited from the recurrent parent, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

Another increasingly popular form of commercial hybrid production involves the use of a mixture of male sterile hybrid seed and male pollinator seed. When planted, the resulting male sterile hybrid plants are pollinated by the pollinator plants. This method is primarily used to produce grain with enhanced quality grain traits, such as high oil, because desired quality grain traits expressed in the pollinator will also be expressed in the grain produced on the male sterile hybrid plant. In this method the desired quality grain trait does not have to be incorporated by lengthy procedures such as recurrent backcross selection into an inbred parent line. One use of this method is described U.S. Pat. Nos. 5, 704,160 and 5,706,603.

There are many important factors to be considered in the art of plant breeding, such as the ability to recognize important morphological and physiological characteristics, the ability to design evaluation techniques for genotypic and phenotypic traits of interest, and the ability to search out and exploit the genes for the desired traits in new or improved combinations.

The objective of commercial maize hybrid line development resulting from a maize plant breeding program is to develop new inbred lines to produce hybrids that combine to produce high grain yields and superior agronomic performance. The primary trait breeders seek is yield. However, many other major agronomic traits are of importance in hybrid combination and have an impact on yield or otherwise provide superior performance in hybrid combinations. Such traits include percent grain moisture at harvest, relative maturity, resistance to stalk breakage, resistance to root lodging, grain quality, and disease and insect resistance. In addition, the lines per se must have acceptable performance for parental traits such as seed yields, kernel sizes, pollen production, all of which affect ability to provide parental lines in sufficient quantity and quality for hybridization. These traits have been shown to be under genetic control and many if not all of the traits are affected by multiple genes.

Pedigree Breeding

The pedigree method of breeding is the mostly widely used methodology for new hybrid line development.

In general terms this procedure consists of crossing two inbred lines to produce the non-segregating F1 generation, and self pollination of the F1 generation to produce the F2 generation that segregates for all factors for which the inbred parents differ. An example of this process is set forth below. Variations of this generalized pedigree method are used, but all these variations produce a segregating generation which contains a range of variation for the traits of interest.

EXAMPLE 1

Hypothetical Example of Pedigree Breeding Program

Consider a cross between two inbred lines that differ for alleles at six loci. The parental genotypes are:

| | |
|---|---|
| Parent 1 | A b C d e F/A b C d e F |
| Parent 2 | a B c D E f/a B c D E f | the F1 from a cross between these two parents is:

| | |
|---|---|
| F1 | A b C d e F/a B C D E f |

Selfing F1 will produce an F2 generation including the following genotypes:

| |
|---|
| A B c D E f/a b C d e F |
| A B c D e f/a b C d E F |
| A B c D e f/a b C d e F |
| . |
| . |

The number of genotypes in the F2 is 36 for six segregating loci (729) and will produce (26)-2 possible new inbreds, (62 for six segregating loci).

Each inbred parent which is used in breeding crosses represents a unique combination of genes, and the combined effects of the genes define the performance of the inbred and its performance in hybrid combination. There is published evidence (Smith, O. S., J. S. C. Smith, S. L. Bowen, R. A. Tenborg and S. J. Wall, *TAG* 80:833-840 (1990)) that each of the lines are different and can be uniquely identified on the basis of genetically-controlled molecular markers.

It has been shown (Hallauer, Amel R. and Miranda, J. B. Fo. Quantitative *Genetics in Maize Breeding*, Iowa State University Press, Ames Iowa, 1981) that most traits of economic value in maize are under the genetic control of multiple genetic loci, and that there are a large number of unique combinations of these genes present in elite maize germplasm. If not, genetic progress using elite inbred lin s would no longer be possible. Studies by Duvick and Russell (Duvick, D. N., *Maydica* 37:6979, (1992); Russell, W. A., *Maydica* XXIX:375-390 (1983)) have shown that over the last 50 years the rate of genetic progress in commercial hybrids has been between one and two percent per year.

The number of genes affecting the trait of primary economic importance in maize, grain yield, has been estimated to be in the range of 10–1000. Inbred lines which are used as parents for breeding crosses differ in the number and combination of these genes. These factors make the plant breeder's task more difficult. Compounding this is evidence that no one line contains the favorable allele at all loci, and that different alleles have different economic values depending on the genetic background and field environment in which the hybrid is grown. Fifty years of breeding experience suggests that there are many genes affecting grain yield and each of these has a relatively small effect on this trait. The effects are small compared to breeders' ability to measure grain yield differences in evaluation trials. Therefore, the parents of the breeding cross must differ at several of these loci so that the genetic differences in the progeny will be large enough that breeders can develop a line that increases the economic worth of its hybrids over that of hybrids made with either parent.

If the number of loci segregating in a cross between two inbred lines is n, the number of unique genotypes in the F2 generation is 3n and the number of unique inbred lines from this cross is $\{(2n)-2\}$. Only a very limited number of these combinations are useful. Only about 1 in 10,000 of the progeny from F2's are commercially useful.

By way of example, if it is assumed that the number of segregating loci in F2 is somewhere between 20 and 50, and that each parent is fixed for half the favorable alleles, it is then possible to calculate the approximate probabilities of finding an inbred that has the favorable allele at $\{(n/2)+m\}$ loci, where n/2 is the number of favorable alleles in each of the parents and m is the number of additional favorable alleles in the new inbred. See Example 2 below. The number m is assumed to be greater than three because each allele has so small an effect that evaluation techniques are not sensitive enough to detect differences due to three or less favorable alleles. The probabilities in Example 2 are on the order of 10-5 or smaller and they are the probabilities that at least one genotype with (n/2)=m favorable alleles will exist.

To put this in perspective, the number of plants grown on 60 million acres (approximate United States corn acreage) at 25,000 plants/acre is 1.5×1012.

EXAMPLE 2

Probability of finding an inbred with m of n favorable alleles.

Assume each parent has n/2 of the favorable alleles and only 1/2 of the combinations of loci are economically useful.

| No. of segregating loci (n) | No. of favorable alleles in Parents (n12) | No. additional favorable alleles in new inbred | Probability that genotype occurs* |
|---|---|---|---|
| 20 | 10 | 14 | 3 × 10−5 |
| 24 | 12 | 16 | 2 × 10−5 |
| 28 | 14 | 18 | 1 × 10−5 |
| 32 | 16 | 20 | 8 × 10−6 |
| 36 | 18 | 22 | 5 × 10−6 |

-continued

| No. of segregating loci (n) | No. of favorable alleles in Parents (n12) | No. additional favorable alleles in new inbred | Probability that genotype occurs* |
|---|---|---|---|
| 40 | 20 | 24 | 3 × 10−6 |
| 44 | 22 | 26 | 2 × 10−6 |
| 48 | 24 | 28 | 1 × 10−6 |

*Probability that a useful combination exists, does not include the probability of identifying this combination if it does exist.

The possibility of having a usably high probability of being able to identify this genotype based on replicated field testing would be most likely smaller than this, and is a function of how large a population of genotypes is tested and how testing resources are allocated in the testing program.

SUMMARY OF THE INVENTION

According to the invention, the is provided a hybrid maize plant, designated as 38A24, produced by crossing two Pioneer Hi-Bred International Inc. proprietary maize lines GE533340 and GE501400. These lines, deposited with the American Type Culture Collection, (ATCC), Manassas Va. 20110, have Accession Number PTA-4287 deposited on May 6, 2002, for GE533340 and Accession Number PTA-1282 deposited on Feb. 3, 2000, for GE501400. This invention thus relates to the hybrid seed 38A24, the hybrid plant produced from the seed, and variants, mutants and trivial modifications of hybrid 38A24 . This invention also relates to methods for producing a maize plant containing in its genetic material one or more transgenes and to the transgenic maize plants produced by that method. This invention further relates to methods for producing maize lines derived from hybrid maize line 38A24 and to the maize lines derived by the use of those methods. This hybrid maize plant is characterized by very high silage yield for its maturity in combination with excellent feeding value and starch concentration.

Definitions

In the description and examples that follow, a number of terms are used herein. In order to provide a clear and consistent understanding of the specification and claims, including the scope to be given such terms, the following definitions are provided. NOTE: ABS is in absolute terms and % MN is percent of the mean for the experiments in which the inbred or hybrid was grown. These designators will follow the descriptors to denot how the values are to be interpreted. Below are the descriptors used in the data tables included herein.

ADF=PERCENT ACID DETERGENT FIBER. The percent of dry matter that is acid detergent fiber in chopped whole plant forage.

ANT ROT=ANTHRACNOSE STALK ROT (*Colletottichum graminicola*). A 1 to 9 visual rating indicating the resistance to Anthracnose Stalk Rot. A higher score indicates a higher resistance.

BAR PLT=BARREN PLANTS. The percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap in paired comparisons and on a 1 to 9 scale (9=highest resistance) in Characteristics Charts.

BU ACR=YIELD (BUSHELS/ACRE). Yield of the grain at harvest in bushels per acre adjusted to 15.5% moisture.

CLN=CORN LETHAL NECROSIS (synergistic interaction of maize chlorotic mottle virus (MCMV) in combination with either maize dwarf mosaic virus (MDMV-A or MDMV-B) or wheat streak mosaic virus (WSMV)). A 1 to 9 visual rating indicating the resistance to Corn Lethal Necrosis. A higher score indicates a higher resistance.

CP=PERCENT OF CRUDE PROTEIN. The percent of dry matter that is crude protein in chopped whole plant forage.

COM RST=COMMON RUST (*Puccinia sorghs*). A 1 to 9 visual rating indicating the resistance to Common Rust. A higher score indicates a higher resistance.

CRM=COMPARATIVE RELATIVE MATURITY (see PRM).

D/D=DRYDOWN. This represents the relative rate at which a hybrid will reach acceptable harvest moisture compared to other hybrids on a 1–9 rating scale. A high score indicates a hybrid that dries relatively fast while a low score indicates a hybrid that dries slowly.

D/E=DROPPED EARS. Represented in a 1 to 9 scale in the Characteristics Chart, where 9 is the rating representing the least, or no, dropped ears.

DIP ERS=DIPLODIA EAR MOLD SCORES (*Diplodia maydis* and *Diplodia macrospora*). A 1 to 9 visual rating indicating the resistance to Diplodia Ear Mold. A higher score indicates a higher resistance.

DM=PERCENT OF DRY MATTER. The percent of dry material in chopped whole plant silage.

DRP EAR=DROPPED EARS. A measure of the number of dropped ears per plot and represents the percentage of plants that did not drop ears prior to harvest.

D/T=DROUGHT TOLERANCE. This represents a 1–9 rating for drought tolerance, and is based on data obtained under stress conditions. A high score indicates good drought tolerance and a low score indicates poor drought tolerance.

EAR HT=EAR HEIGHT. The ear height is a measure from the ground to the highest placed developed ear node attachment and is measured in inches. This is represented in a 1 to 9 scale in the Characteristics Chart, where 9 is highest.

EAR MLD=General Ear Mold. Visual rating (1–9 score) where a "1" is very susceptible and a "9" is very resistant. This is based on overall rating for ear mold of mature ears without determining the specific mold organism, and may not be predictive for a specific ear mold.

EAR SZ=EAR SIZE. A 1 to 9 visual rating of ear size. The higher the rating the larger the ear size.

ECB 1LF=EUROPEAN CORN BORER FIRST GENERATION LEAF FEEDING (*Ostinnia nubilalis*). A 1 to 9 visual rating indicating the resistance to preflowering leaf feeding by first generation European Corn Borer. A higher score indicates a higher resistance.

EECB 2IT=EUROPEAN CORN BORER SECOND GENERATION INCHES OF TUNNELING (*Ostrinia nubilalis*). Average inches of tunneling per plant in the stalk.

ECB 2SC=EUROPEAN CORN BORER SECOND GENERATION (*Ostrinia nubilalis*). A 1 to 9 visual rating indicating post flowering degree of stalk breakage and other evidence of feeding by European Corn Borer, Second Generation. A higher score indicates a higher resistance.

ECB DPE=EUROPEAN CORN BORER DROPPED EARS (*Ostrinia nubilalis*). Dropped ears due to European Corn Borer. Percentage of plants that did not drop ears under second generation corn borer infestation.

E/G=EARLY GROWTH. This represents a 1 to 9 rating for early growth, scored when two leaf collars are visible.

EGRWTH=EARLY GROWTH. The relative height and size of a corn seedling at the 24 leaf stage of growth. This is a visual rating (1 to 9), with 1 being weak or slow growth, 5 being average growth and 9 being strong growth. Taller plants, wider leaves, more green mass and darker color constitute higher scores.

EST CNT=EARLY STAND COUNT. This is a measure of the stand establishment in the spring and r presents the number of plants that emerge on per plot basis for the inbred or hybrid.

EYE SPT=Eye Spot (*Kabatiella zeae* or *Aureobasidium zeae*). A 1 to 9 visual rating indicating the resistance to Eye Spot. A higher score indicates a higher resistance.

FUS ERS=FUSARIUM EAR ROT SCORE (*Fusarum moniliforme* or *Fusarium subglutinans*). A 1 to 9 visual rating indicating the resistance to Fusarium ear rot. A higher score indicates a higher resistance.

G/A=GRAIN APPEARANCE. Appearance of grain in the grain tank (scored down for mold, cracks, red streak, etc.).

GDU=Growing Degree Units. Using the Barger Heat Unit Theory, that assumes that maize growth occurs in the temperature range 50° F.–86° F. and that temperatures outside this range slow down growth; the maximum daily heat unit accumulation is 36 and the minimum daily heat unit accumulation is 0. The seasonal accumulation of GDU is a major factor in determining maturity zones.

GDU PHY=GDU TO PHYSIOLOGICAL MATURITY. The number of growing degree units required for an inbred or hybrid line to have approximately 50 percent of plants at physiological maturity from time of planting. Growing degree units are calculated by the Barger method.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{MAX. temp.} + \text{Min. temp.})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GIB ERS=GIBBERELLA EAR ROT (PINK MOLD) (*Gibberella zeae*). A 1 to 9 visual rating indicating the resistance to Gibberella Ear Rot. A higher score indicates a higher resistance.

GLF SPT=Gray Leaf Spot (*Cercospora zeae-maydis*). A 1 to 9 visual rating indicating the resistance to Gray Leaf Spot. A higher score indicates a higher resistance.

GOS WLT=Goss' Wilt (*Corynebactenum nebraskense*). A 1 to 9 visual rating indicating the resistance to Goss' Wilt. A higher score indicates a higher resistance.

GRN APP=GRAIN APPEARANCE. This is a 1 to 9 rating for the general appearance of the shelled grain as it is harvested based on such factors as the color of harvested grain, any mold on the grain, and any cracked grain. High scores indicate good grain quality.

H/POP=YIELD AT HIGH DENSITY. Yield ability at relatively high plant densities on 1–9 relative rating system with a higher number indicating the hybrid responds well to high plant densities for yield relative to other hybrids. A 1, 5, and 9 would represent very poor, average, and very good yield response, respectively, to increased plant density.

HC BLT=HELMINTHOSPORIUM CARBONUM LEAF BLIGHT (*Helminthosporium carbonum*). A 1 to 9 visual rating indicating the resistance to Helminthosporium infection. A higher score indicates a higher resistance.

HD SMT=Head Smut (*Sphacelotheca reiliana*). This score indicates the percentage of plants not infected.

INC D/A=GROSS INCOME (DOLLARS PER ACRE). Relative income per acre assuming drying costs of two cents per point above 15.5 percent harvest moisture and current market price per bushel.

INCOME/ACRE. Income advantage of hybrid to be patented over other hybrid on per acre basis.

INC ADV=GROSS INCOME ADVANTAGE. GROSS INCOME advantage of variety #1 over variety #2.

L/POP=YIELD AT LOW DENSITY. Yield ability at relatively low plant densities on a 1–9 relative system with a higher number indicating the hybrid responds well to low plant densities for yield relative to other hybrids. A 1, 5, and 9 would represent very poor, average, and very good yield response, respectively, to low plant density.

MDM CPX=Maize Dwarf Mosaic Complex (MDMV= Maize Dwarf Mosaic Virus and MCDV=Maize Chlorotic Dwarf Virus). A 1 to 9 visual rating indicating the resistance to Maize Dwarf Mosaic Complex. A higher score indicates a higher resistance.

MST=HARVEST MOISTURE. The moisture is the actual percentage moisture of the grain at harvest.

MST ADV=MOISTURE ADVANTAGE. The moisture advantage of variety #1 over variety #2 as calculated by: MOISTURE of variety #2 −MOISTURE of variety #1 =MOISTURE ADVANTAGE of variety #1.

NLF BLT=Northern Leaf Blight (*Helminthosporium turicum* or *Exserohilum turcicum*). A 1 to 9 visual rating indicating the resistance to Northern Leaf Blight. A higher score indicates a higher resistance.

OIL=GRAIN OIL. The amount of the kernel that is oil, expressed as a percentage on a dry weight basis.

OILT=GRAIN OIL. Absolute value of oil content of the kernel as predicted by Near-infrared Transmittance and expressed as a percent of dry matter.

PHY CRM=CRM at physiological maturity.

PLT HT=PLANT HEIGHT. This is a measure of the height of the plant from the ground to the tip of the tassel in inches. This is represented as a 1 to 9 scale, 9 highest, in the Characteristics Chart.

POL SC=POLLEN SCORE. A 1 to 9 visual rating indicating the amount of pollen shed. The higher the score the more pollen shed.

POL WT=POLLEN WEIGHT. This is calculated by dry weight of tassels collected as shedding commences minus dry weight from similar tassels harvested after shedding is complete.

It should be understood that the inbred can, through routine manipulation of cytoplasmic or other factors, be produced in a male-sterile form. Such embodiments are also contemplated within the scope of the present claims.

POP K/A=PLANT POPULATIONS. Measured as 1000 s per acre.

POP ADV=PLANT POPULATION ADVANTAGE. The plant population advantage of variety #1 over variety #2 as calculated by PLANT POPULATION of variety #2 −PLANT POPULATION of variety #1 =PLANT POPULATION ADVANTAGE of variety #1.

PRM=PREDICTED Relative Maturity. This trait, predicted relative maturity, is based on the harvest moisture of the grain. The relative maturity rating is based on a known set of checks and utilizes standard linear regression analyses and is referred to as the Comparative Relative Maturity Rating System that is similar to the Minnesota Relative Maturity Rating System.

PRM SHb=A relative measure of the growing degree units (GDU) required to reach 50% pollen shed. Relative values are predicted values from the linear regression of observed GDU's on relative maturity of commercial checks.

PRO=PROTEIN RATING . Rating on a 1 to 9 scale comparing relative amount of protein in the grain compared to hybrids of similar maturity. A "1" score difference represents a 0.4 point change in grain protein percent (e.g., 8.0% to 8.4%).

PROT=GRAIN PROTEIN. Absolute value of protein content of the kernel as predicted by Near-Infrared Transmittance and expressed as a percent of dry matter.

PROTEIN=GRAIN PROTEIN. The amount of the kernel that is crude protein, express d as a percentage on a dry weight basis.

P/Y=PROTEIN/YIELD RATING. Indicates, on a 1 to 9 scale, the economic value of a hybrid for swine and poultry feeders. This takes into account the income due to yield, moisture and protein content.

ROOTS (%)=Percent of stalks NOT root lodged at harvest.

R/L=ROOT LODGING. A 1 to 9 rating indicating the level of root lodging resistance. The higher score represents higher levels of resistance.

RT LDG=ROOT LODGING. Root lodging is the percentage of plants that do not root lodge; plants that lean from the vertical axis as an approximately 300 angle or greater would be counted as root lodged.

RTL ADV=ROOT LODGING ADVANTAGE. The root lodging advantage of variety #1 over variety #2.

S/L=STALK LODGING. A 1 to 9 rating indicating the level of stalk lodging resistance. The higher scores represent higher levels of resistance.

SCT GRN=SCATTER GRAIN. A 1 to 9 visual rating indicating the amount of scatter grain (lack of pollination or kernel abortion) on the ear. The higher the score the less scatter grain.

SEL IND=SELECTION INDEX. The selection index gives a single measure of the hybrid's worth based on information for up to five traits. A maize breeder may utilize his or her own set of traits for the selection index. One of the traits that is almost always included is yield. The selection index data presented in the tables represent the mean value averaged across testing stations.

SIL DMP=SILAGE DRY MATTER. The percent of dry material in chopped whole plant silage.

SLF BLT=SOUTHERN LEAF BLIGHT (*Helminthosporium maydis* or *Bipolaris maydis*). A 1 to 9 visual rating indicating the resistance to Southern Leaf Blight. A higher score indicates a higher resistance.

SLK CRM=CRM at Silking.

SOU RST=SOUTHERN RUST (Puccinia polysora). A 1 to 9 visual rating indicating the resistance to Southern Rust. A higher score indicates a higher resistance.

STA GRN=STAY GREEN. Stay green is the measure of plant health near the time of black layer formation (physiological maturity). A high score indicates better late-season plant health.

STAND (%)=Percent of stalks standing at harvest.

STARCH=PERCENT OF STARCH. The percent of dry matter that is starch in chopp d whole plant forage.

STD ADV=STALK STANDING ADVANTAGE. The advantage of variety #1 over variety #2 for the trait STK CNT.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

STR RVVH=PERCENT OF STARCH. This is the percent of dry matter that is starch in chopped whole plant forage as predicted by Near Infrared Spectroscopy.

STRT=GRAIN STARCH. Absolute value of starch content of the kernel as predicted by Near-Infrared Transmittance and expressed as a percent of dry matter.

STW WLT=Stewart's Wilt (*Erwinia stewartii*). A 1 to 9 visual rating indicating the resistance to Stewart's Wilt. A higher score indicates a higher resistance.

TAS BLS=TASSEL BLAST, A 1 to 9 visual rating was used to measure the degree of blasting (necrosis due to heat stress) of the tassel at the time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TDM/HA=TOTAL DRY MATTER PER HECTARE. Yield of total dry plant material in metric tons per hectare.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TIL LER=TILLERS. A count of the number of tillers per plot that could possibly shed pollen was taken. Data are given as a percentage of tillers: number of tillers per plot divided by number of plants per plot.

TST WT (CHARACTERISTICS CHART)=Test weight on a 1 to 9 rating scale with a 9 being the highest rating.

TST WT=TEST WEIGHT (UNADJUSTED). The measure of the weight of the grain in pounds for a given volume (bushel).

TST WTA=TEST WEIGHT ADJUSTED. The measure of the weight of the grain in pounds for a given volume (bushel) adjusted for 15.5 percent moisture.

TSW ADV=TEST WEIGHT ADVANTAGE. The test weight advantage of variety #1 over variety #2.

WIN M%=PERCENT MOISTURE WINS.

WIN Y%=PERCENT YIELD WINS.

YIELD=YIELD OF SILAGE. Yield in tons per acre at 30% dry matter.

YLD=YIELD. It is the same as BU ACR ABS.

YLD ADV=YIELD ADVANTAGE. The yield advantage of variety #1 over variety #2 as calculated by: YIELD of variety #1 −YIELD variety #2 =yield advantage of variety #1.

YLD SC=YIELD SCORE. A 1 to 9 visual rating was used to give a relative rating for yield based on plot ear piles. The higher the rating the greater visual yield appearance.

DETAILED DESCRIPTION OF THE INVENTION

Pioneer Brand Hybrid 38A24 has exceptional yield with above average dry down. The hybrid shows above average late season plant health and consistent yield performance under seasonal drought and high temperature stress. Hybrid 38A24 exhibits above average early season growth as well as above average test weight and grain quality. The hybrid demonstrates solid resistance to Northern Leaf Blight, Goss's Wilt, and Stewart's Wilt. It also exhibits excellent resistance to head smut, with exceptional silage yield potential, superior readily available energy and whole plant digestability. 38A24 is particularly suited to the Northwest, Northcentral, Northeast, Western, and Drylands regions of the United States, Canada, and Western Europe.

Pioneer Brand Hybrid 38A24 is a single cross, yellow endosperm, dent maize hybrid. Hybrid 38A24 has a relative maturity of approximately 96 based on the Comparative Relative Maturity Rating System for harvest moisture of grain.

This hybrid has the following characteristics based on the data collected primarily at Johnston, Iowa.

TABLE 1

VARIETY DESCRIPTION INFORMATION
VARIETY = 38A24

1 TYPE: (describe intermediate types in Comments section):
2    1 = Sweet   2 = Dent   3 = Flint   4 = Flour
     5 = Pop   6 = Ornamental
2. MATURITY:

| DAYS | HEAT UNITS | |
|---|---|---|
| 064 | 1,134.3 | From emergence to 50% of plants in silk |
| 065 | 1,171.0 | From emergence to 50% of plants in pollen |
| 002 | 0,060.7 | From 10% to 90% pollen shed |
| | | From 50% silk to harvest at 25% moisture |

3. PLANT:

| | | | Standard Deviation | Sample Size |
|---|---|---|---|---|
| 0,249.7 | cm | Plant Height (to tassel tip) | 12.66 | 15 |
| 0,093.0 | cm | Ear Height (to base of top ear node) | 5.00 | 15 |
| 0,016.2 | cm | Length of Top Ear Internode | 1.25 | 15 |
| 0.0 | | Average Number of Tillers | 0.00 | 3 |
| 1.0 | | Average Number of Ears per Stalk | 0.06 | 3 |
| 2.0 | | Anthocyanin of Brace Roots: 1 = Absent   2 = Faint 3 = Moderate   4 = Dark | | |

4. LEAF:

| | | | Standard Deviation | Sample Size |
|---|---|---|---|---|
| 009.3 | cm | Width of Ear Node Leaf | 0.12 | 15 |
| 092.1 | cm | Length of Ear Node Leaf | 3.06 | 15 |
| 06.2 | | Number of leaves above too ear | 0.53 | 15 |
| 019.3 | | Degrees Leaf Angle (measure from 2nd leaf above ear at anthesis to stalk above leaf) | 5.93 | 15 |
| 03 | | Leaf Color   Dark Green   (Munsell code)   5GY34 | | |
| 1.0 | | Leaf Sheath Pubescence (Rate on scale from 1 = none to 9 = like peach fuzz) | | |
| | | Marginal Waves (Rate on scale from 1 = none to 9 = many) | | |
| | | Longitudinal Creases (Rate an scale from 1 = none to 9 = many) | | |

5. TASSEL:

| | | Standard Deviation | Sample Size |
|---|---|---|---|
| 07.5 | Number of Primary Lateral Branches | 1.03 | 15 |
| 022.9 | Branch Angle from Central Spike | 6.65 | 15 |
| 57.5 cm | Tassel Length (from top leaf collar to tassel tip) | 3.06 | 15 |
| 7.0 | Pollen Shed (rate on scale from 0 = male sterile to 9 = heavy shed) | | |
| 11 | Anther Color   Pink   (Munsell code)   10RP58 | | |
| 01 | Glume Color   Light Green   (Munsell code)   5GY56 | | |
| 1.0 | Bar Glumes (Glume Bands): 1 = Absent 2 = Present | | |
| 18 cm | Peduncle Length (cm. from top leaf to basal branches) | | |

6a. EAR (Unhusked Data):
11   Silk Color (3 days after emergence)    Pink      (Munsell code)   10R76
1    Fresh Husk Color (25 days after 50% silking)   Light Green    (Munsell code)   5GY68
21   Dry Husk color (65 days after 50% silking)    Buff      (Munsell code)   2.5Y92
2    Position of Ear at Dry Husk Stage: 1 = Upright 2 = Horizontal   Horizontal 3 = Pendant

TABLE 1-continued

VARIETY DESCRIPTION INFORMATION
VARIETY = 38A24

| | | | | | |
|---|---|---|---|---|---|
| 6 | | Husk Tightness (Rate of Scale from 1 = very loose to 9 = very tight) | | | |
| 2 | | Husk Extension (at harvest): 1 = Short (ears exposed) 2 = Medium (<8 cm) 3 = Long (8–10 cm beyond ear tip) 4 = Very Long (>10 cm) | | | Medium |

6b. EAR (Husked Ear Data):

| | | | Standard Deviation | Sample Size | |
|---|---|---|---|---|---|
| 18 | cm | Ear Length | 0.58 | 15 | |
| 43 | mm | Ear Diameter at mid-point | 0.58 | 15 | |
| 189 | gm | Ear Weight | 2.00 | 15 | |
| 15 | | Number of Kernel Rows | 1.00 | 15 | |
| 2 | | Kernel Rows: 1 = Indistinct 2 = Distinct | | | Distinct |
| 2 | | Row Alignment 1 = Straight 2 = Slightly Curved 3 = Spiral | | | Slightly Curved |
| 11 | cm | Shank Length | 1.73 | 15 | |
| 2 | | Ear Taper: 1 = Slight 2 = Average 3 = Extreme | | | Average |

7. KERNEL (Dried):

| | | | Standard Deviation | Sample Size | |
|---|---|---|---|---|---|
| 11 | mm | Kernel Length | 0.58 | 15 | |
| 8 | mm | Kernel Width | 0.58 | 15 | |
| 5 | mm | Kernel Thickness | 0.00 | 15 | |
| 47 | | % Round Kernels (Shape Grade) | 7.51 | 3 | |
| 1 | | Aleurone Color Pattern: 1 = Homozygous 2 = Segregating | | | Homozygous |
| 7 | | Aleurone Color Yellow | (Munsell code) | | 10YR714 |
| 7 | | Hard Endosperm Color Yellow | (Munsell code) | | 1.25Y712 |
| 3 | | Endosperm Type: Normal Starch 1 = Sweet (Sul) 2 = Extra Sweet (sh2) 3 = Normal Starch 4 = High Amylose Starch 5 = Waxy Starch 6 = High Protein 7 = High Lysine 8 = Super Sweet (se) 9 = High Oil 10 = Other _____ | | | |
| 36 | gm | Weight per 100 Kernels (unsized sample) | 1.53 | 3 | |

8. COB:

| | | | Standard Deviation | Sample Size | |
|---|---|---|---|---|---|
| 24 | mm | Cob Diameter at midpoint | 0.58 | 15 | |
| 14 | | Cob Color Red | (Munsell code) | | 10R36 |

9. DISEASE RESISTANCE (Rate from 1 (most susceptible) to 9 (most resistant): leave blank if not tested; leave Race or Strain Options blank if polygenic):

A. Leaf Blight, Wilts, and Local Infection Diseases
    Anthracnose Leaf Blight (*Colletotrichum graminicola*)
    Common Rust (*Puccinia sorghi*)
    Common Smut (*Ustilago maydis*)
  6 Eyespot (*Kabatiella zeae*)
  7 Goss's Wilt (*Clavibacter michiganense* spp. *nebraskense*)
  6 Gray Leaf Spot (*Cercospora zeae-maydis*)
    Helminthosporium Leaf Spot (*Bipolaris zeicola*) Race _____
  7 Northern Leaf Blight (*Exserohilum turcicum*) Race _____
    Southern Leaf Blight (*Bipolaris maydis*) Race _____
    Southern Rust (*Puccinia polysora*)
  8 Stewart's Wilt (*Erwinia stewartii*)
    Other (Specify) _____

B. Systemic Diseases
    Corn Lethal Necross (MCMV and MDMV)
    Head Smut (*Sphacelotheca reiliana*)
    Maize Chlorotic Dwarf Virus (MDV)
    Maize Chlorotic Mottle Virus (MCMV)
    Maize Dwarf Mosaic Virus (MDMV)
    Sorghum Downy Mildew of Corn (*Peronosclerospora sorghi*)
    Other (Specify) _____

C. Stalk Rots
  5 Anthracnose Stalk Rot (*Colletotrichum graminicola*)
    Diplodia Stalk Rot (*Stenocarpella maydis*)
    Fusarium Stalk Rot (*Fusarium monlliforme*)
    Gibberella Stalk Rot (*Gibberella zeae*)
    Other (Specify) _____

D. Ear and Kernel Rots
    Aspergillus Ear and Kernel Rot (*Aspergillus flavus*)
    Diplodia Ear Rot (*Stenocarpella maydis*)
  6 Fusarium Ear and Kernel Rot (*Fusarium monlliforme*)
  4 Gibberella Ear Rot (*Gibberella zeae*)
    Other (Specify) _____

10. INSECT RESISTANCE (Rate from 1 (most susceptible) to 9 (most resistant); (leave blank if not tested):
    Banks grass Mite (*Oligonychus pratensis*)
    Corn Worm (*Helicoverpa zea*)
      Leaf Feeding
      Silk Feeding
        mg larval wt
      Ear Damage
    Cam Leaf Aphid (*Rhopalosiphum maidis*)
    Corn Sap beetle (*Carpophilius dimidiatus*)
    European Corn Borer (*Ostrinia nubilalis*)
    5 1st Generation (Typically Whorl Leaf Feeding)
    7 2nd Generation (Typically Leaf Sheath-Collar Feeding)
      Stalk Tunneling
      cm tunneled/plant
    Fall Armyworm (*Spodoptera fruqiperda*)
      Leaf Feeding
      Silk Feeding
      mg larval wt
    Maize Weevil (*Sitophilus zeamaize*)
    Northern Rootworm (*Diabrotica barberi*)
    Southern Rootworm (*Diabrotica undecimpunctata*)
    Southwestern Corn Borer (*Diatreaea grandiosella*)
      Leaf Feeding
      Stalk Tunneling
      cm tunneled/plant
    Two-spotted Spider Mite (*Tetranychus urticae*)
    Western Rootworm (*Diabrotica virgifrea virgifera*)
    Other (Specify) _____

11. AGRONOMIC TRAITS:
    6 Staygreen (at 65 days after anthesis)
      (Rate on a scale from 1 = worst to 9 = excellent)
    0.0 % Dropped Ears (at 65 days after anthesis)
      % Pre-anthesis Brittle Snapping
      % Pre-anthesis Root Lodging
    11.6 Post-anthesis Root Lodging (at 65 days after anthesis)
    11,693 Kg/ha Yield (at 12–13% grain moisture)

*In interpreting the foregoing color designations. reference may be made to the Munsell Glossy Book of Color, a standard color reference.

Research Comparisons for Pioneer Hybrid 38A24

Comparisons of characteristics for Pioneer Brand Hybrid 38A24 were made against Pioneer Brand Hybrids 38P05, 37M81, 37H24, 3752, and 38N40 all of which are hybrids with similar maturity and have a similar area of adaptation to hybrid 38A24.

Table 2A compares Pioneer Brand Hybrid 38A24 and Pioneer Brand Hybrid 38P05. According to the results, hybrid 38A24 is significantly higher yielding than hybrid 38P05. Hybrid 3BA24 further demonstrates significantly superior early growth as well as significantly better stay green than hybrid 38P05. 38A24 also shows significantly better resistance to stalk lodging and significantly more husk cover than 38P05. Hybrid 38A24 is later to flower, with a significantly higher number of growing degree units to pollen shed and to silk than hybrid 38P05.

Table 2B compares Pioneer Brand Hybrid 38A24 and Pioneer Brand Hybrid 37M81. The table indicates that hybrid 38A24 is significantly higher yielding than hybrid 37M81. Hybrid 38A24 exhibits a significantly higher test weight and significantly superior root lodging resistance than hybrid 37M81. 38A24 further demonstrates significantly superior resistance to stalk lodging and significantly better stay green than hybrid 37M81. 38A24 also shows significantly better resistance to Stewart's Wilt and significantly larger husk cover than hybrid 37M81. 38A24 is later to flower, with significantly higher number of growing degree units to pollen shed and to silk than hybrid 37M81, but fills the grain quickly and dries to reach a similar moister at harvest, despite the later flowering date.

Table 2C compares Pioneer Brand Hybrid 38A24 and Pioneer Brand Hybrid 37H24. According to the results, hybrid 38A24 is significantly higher yielding than hybrid 37H24. Hybrid 38A24 further demonstrates significantly superior early growth as well as significantly better resistance to stalk lodging than hybrid 37H24. Hybrid 38A24 also exhibits significantly taller plant stature and significantly better resistance to Anthracnose stalk rot than hybrid 37H24. 38A24 further exhibits significantly better tolerance to Eye Spot and is later to flower, with a significantly higher number of growing degree units to pollen shed and to silk than hybrid 37H24.

Table 2D compares Pioneer Brand Hybrid 38A24 and Pioneer Brand Hybrid 3752. The table indicates than hybrid 38A24 is significantly higher yielding with significantly lower harvest moisture and a significantly higher test weight than hybrid 3752. Hybrid 38A24 further demonstrates significantly superior early growth as well as significantly better resistance to stalk lodging than hybrid 3752. Hybrid 3BA24 shows significantly better stay green and a significantly higher stand establishment count than hybrid 3752. 38A24 further exhibits significantly superior resistance to Anthracnose stalk rot and significantly larger husk cover than hybrid 3752. 38A24 exhibits significantly better Stewart's Wilt resistance and is later to flower, with a significantly higher number of growing degree units to pollen shed and to silk than hybrid 3752.

Table 2E compares Pioneer Brand Hybrid 38A24 and Pioneer Brand Hybrid 38N40. The table evidences that hybrid 38A24 is significantly higher yielding than hybrid 38N40. Hybrid 38A24 further demonstrates significantly higher harvest moisture but has a significantly higher test weight than hybrid 38N40. Hybrid 38A24 exhibits significantly early growth as well as significantly better resistance to stalk lodging than hybrid 38N40. Hybrid 38A24 also shows a significantly better stay green score and significantly superior early coverage than hybrid 38N40. 38H24 further exhibits significantly better tolerance to Stewart's Wilt and is later to flower, with a significantly higher number to growing degree units to pollen shed and to silk when compared to hybrid 38N40.

TABLE 2A

HYBRID COMPARISON REPORT
VARIETY #1 = 38A24
VARIETY #2 = 38P05

|  | PRM ABS | PRM SHD ABS | BU ACR ABS | BU ACR % MN | MST % MN | TST WT ABS | EGR WTH % MN | EST CNT % MN | GDU SHD % MN |
|---|---|---|---|---|---|---|---|---|---|
| TOTAL SUM | | | | | | | | | |
| 1 | 96 | 100 | 186.8 | 106 | 101 | 56.4 | 102 | 106 | 102 |
| 2 | 94 | 96 | 178.8 | 102 | 94 | 56.8 | 96 | 99 | 99 |
| LOCS | 2 | 2 | 136 | 138 | 139 | 56 | 55 | 7 | 50 |
| REPS | 2 | 2 | 140 | 140 | 141 | 58 | 55 | 7 | 59 |
| DIFF | 3 | 4 | 8.0 | 4 | 7 | 0.4 | 6 | 7 | 3 |
| PR > T | .131 | .095* | .000# | .000# | .000# | .158 | .018+ | .184 | .000# |
|  | GDU SLK % MN | STK CNT % MN | PLT HT % MN | EAR HT % MN | RT LDG % MN | STA GRN % MN | STK LDG % MN | BRT STK % MN | DRP EAR % MN |
| TOTAL SUM | | | | | | | | | |
| 1 | 101 | 100 | 99 | 97 | 104 | 122 | 101 | 101 | 100 |
| 2 | 99 | 101 | 97 | 93 | 112 | 101 | 104 | 101 | 100 |
| LOCS | 40 | 203 | 62 | 60 | 36 | 62 | 78 | 23 | 10 |
| REPS | 45 | 264 | 68 | 65 | 37 | 64 | 78 | 23 | 10 |
| DIFF | 3 | 0 | 2 | 4 | 8 | 22 | 3 | 0 | 0 |
| PR > T | .000# | .999 | .002# | .001# | .051* | .000# | .005# | .999 | .999 |
|  | GLF SPT ABS | NLF BLT ABS | GOS WLT ABS | STW WLT ABS | ANT ROT ABS | HD SMT ABS | FUS ERS ABS | GIB ERS ABS | EYE SPT ABS |
| TOTAL SUM | | | | | | | | | |
| 1 | 5.5 | 7.3 | 7.3 | 7.8 | 4.5 | 99.2 | 5.8 | 4.8 | 6.0 |
| 2 | 4.5 | 6.5 | 7.0 | 7.5 | 2.0 | 96.2 | 5.8 | 5.5 | 5.6 |
| LOCS | 2 | 6 | 2 | 4 | 2 | 3 | 9 | 6 | 4 |
| REPS | 3 | 9 | 4 | 4 | 4 | 6 | 9 | 9 | 6 |
| DIFF | 1.0 | 0.8 | 0.3 | 0.3 | 2.5 | 3.0 | 0.0 | 0.7 | 0.4 |
| PR > T | .500 | .248 | .500 | .638 | .126 | .423 | .999 | .371 | .486 |

TABLE 2A-continued

HYBRID COMPARISON REPORT
VARIETY #1 = 38A24
VARIETY #2 = 38P05

|  | ECB 1LF ABS | ECB 2SC ABS | HSK CVR ABS | HSK CVR % MN | OIL T ABS | PRO T ABS | STR T ABS |
|---|---|---|---|---|---|---|---|
| TOTAL SUM |  |  |  |  |  |  |  |
| 1 | 5.1 | 7.4 | 6.4 | 131 | 4.3 | 10.3 | 71.0 |
| 2 | 4.9 | 6.7 | 5.2 | 106 | 4.4 | 9.0 | 70.2 |
| LOCS | 4 | 9 | 28 | 28 | 2 | 2 | 2 |
| REPS | 6 | 10 | 28 | 28 | 2 | 2 | 2 |
| DIFF | 0.3 | 0.7 | 1.2 | 26 | 0.2 | 1.3 | 0.8 |
| PR > T | .391 | .122 | .001# | .001# | .674 | .311 | .610 |

*10% SIG
+5% SIG
1% SIG

TABLE 2B

HYBRID COMPARISON REPORT
VARIETY #1 = 38A24
VARIETY #2 = 37M81

|  | PRM ABS | PRM SHD ABS | BU ACR ABS | BU ACR % MN | MST % MN | TST WT ABS | EGR WTH % MN | EST CNT % MN | GDU SHD % MN |
|---|---|---|---|---|---|---|---|---|---|
| TOTAL SUM |  |  |  |  |  |  |  |  |  |
| 1 | 96 | 100 | 185.5 | 106 | 100 | 56.0 | 104 | 102 | 102 |
| 2 | 96 | 97 | 175.3 | 100 | 100 | 53.6 | 101 | 107 | 100 |
| LOCS | 4 | 3 | 159 | 159 | 160 | 68 | 64 | 20 | 56 |
| REPS | 4 | 3 | 163 | 163 | 163 | 71 | 64 | 20 | 65 |
| DIFF | 0 | 3 | 10.3 | 6 | 1 | 2.4 | 3 | 5 | 2 |
| PR > T | .999 | .039+ | .000# | .000# | .276 | .000# | .270 | .039+ | .000# |

|  | GDU SLK % MN | STK CNT % MN | PLT HT % MN | EAR HT % MN | RT LDG % MN | STA GRN % MN | STK LDG % MN | BRT STK % MN | DRP EAR % MN |
|---|---|---|---|---|---|---|---|---|---|
| TOTAL SUM |  |  |  |  |  |  |  |  |  |
| 1 | 101 | 101 | 99 | 97 | 103 | 120 | 103 | 101 | 100 |
| 2 | 99 | 102 | 101 | 103 | 95 | 96 | 101 | 101 | 100 |
| LOCS | 42 | 229 | 68 | 67 | 41 | 75 | 91 | 28 | 17 |
| REPS | 47 | 291 | 75 | 73 | 42 | 77 | 91 | 28 | 17 |
| DIFF | 2 | 2 | i | 6 | 8 | 24 | 2 | 0 | 1 |
| PR > T | .000# | .000# | .062* | .000# | .047+ | .000# | .032+ | .999 | .090* |

|  | GLF SPT ABS | NLF BLT ABS | GOS WLT ABS | STW WLT ABS | ANT ROT ABS | HD SMT ABS | FUS ERS ABS | GIB ERS ABS | EYE SPT ABS |
|---|---|---|---|---|---|---|---|---|---|
| TOTAL SUM |  |  |  |  |  |  |  |  |  |
| 1 | 5.5 | 7.3 | 7.3 | 7.8 | 4.5 | 99.2 | 5.8 | 4.8 | 5.8 |
| 2 | 5.8 | 7.1 | 7.3 | 5.0 | 4.8 | 97.2 | 5.9 | 5.4 | 6.0 |
| LOCS | 2 | 6 | 2 | 4 | 2 | 3 | 9 | 5 | 4 |
| REPS | 3 | 9 | 4 | 4 | 4 | 6 | 9 | 8 | 5 |
| DIFF | 0.3 | 0.2 | 0.0 | 2.8 | 0.3 | 2.0 | 0.1 | 0.6 | 0.3 |
| PR > T | .795 | .695 | .999 | .035+ | .874 | .072* | .799 | .501 | .718 |

|  | ECB 1LF ABS | ECB 2SC ABS | HSK CVR ABS | HSK CVR % MN | OIL T ABS | PRO T ABS | STR T ABS |
|---|---|---|---|---|---|---|---|
| TOTAL SUM |  |  |  |  |  |  |  |
| 1 | 5.1 | 7.4 | 6.3 | 127 | 4.3 | 10.3 | 71.0 |
| 2 | 4.6 | 6.4 | 4.9 | 94 | 4.7 | 9.3 | 70.2 |
| LOCS | 4 | 9 | 34 | 34 | 2 | 2 | 2 |
| REPS | 6 | 10 | 34 | 34 | 2 | 2 | 2 |

TABLE 2B-continued

HYBRID COMPARISON REPORT
VARIETY #1 = 38A24
VARIETY #2 = 37M81

|      | DIFF  | 0.5   | 1.0  | 1.5   | 33    | 0.5  | 0.9  | 0.7  |
|------|-------|-------|------|-------|-------|------|------|------|
|      | PR > T| .092+ | .147 | .000# | .001# | .376 | .236 | .597 |

*10% SIG
+5% SIG
1% SIG

TABLE 2C

HYBRID COMPARISON REPORT
VARIETY #1 = 38A24
VARIETY #2 = 37H24

|           | PRM ABS | PRM SHD ABS | BU ACR ABS | BU ACR % MN | MST % MN | TST WT ABS | EGR WTH % MN | EST CNT % MN | GDU SHD % MN |
|-----------|---------|-------------|------------|-------------|----------|------------|--------------|--------------|--------------|
| TOTAL SUM |         |             |            |             |          |            |              |              |              |
| 1         | 96      | 100         | 189.4      | 106         | 101      | 56.5       | 101          | 106          | 102          |
| 2         | 97      | 97          | 184.7      | 103         | 102      | 57.1       | 94           | 103          | 100          |
| LOCS      | 2       | 2           | 151        | 151         | 152      | 57         | 66           | 7            | 50           |
| REPS      | 2       | 2           | 153        | 153         | 154      | 59         | 66           | 7            | 59           |
| DIFF      | 1       | 3           | 4.7        | 3           | 2        | 0.6        | 7            | 2            | 2            |
| PR > T    | .035+   | .144        | .001#      | .002#       | .000#    | .013+      | .005#        | .627         | .000#        |

|           | GDU SLK % MN | STK CNT % MN | PLT HT % MN | EAR HT % MN | RT LDG % MN | STA GRN % MN | STK LDG % MN | BRT STK % MN | DRP EAR % MN |
|-----------|--------------|--------------|-------------|-------------|-------------|--------------|--------------|--------------|--------------|
| TOTAL SUM |              |              |             |             |             |              |              |              |              |
| 1         | 101          | 101          | 99          | 98          | 104         | 122          | 103          | 101          | 100          |
| 2         | 100          | 101          | 96          | 96          | 103         | 114          | 99           | 102          | 100          |
| LOCS      | 40           | 217          | 73          | 72          | 36          | 63           | 91           | 22           | 10           |
| REPS      | 45           | 278          | 79          | 77          | 37          | 65           | 91           | 22           | 10           |
| DIFF      | 2            | 0            | 3           | 2           | 0           | 8            | 4            | 1            | 0            |
| PR > T    | .000#        | .999         | .000#       | .065*       | .999        | .240         | .001#        | .049+        | .999         |

|           | GLF SPT ABS | NLF BLT ABS | GOS WLT ABS | STW WLT ABS | ANT ROT ABS | HD SMT ABS | FUS ERS ABS | GIB ERS ABS | EYE SPT ABS |
|-----------|-------------|-------------|-------------|-------------|-------------|------------|-------------|-------------|-------------|
| TOTAL SUM |             |             |             |             |             |            |             |             |             |
| 1         | 5.5         | 6.9         | 7.3         | 7.8         | 4.5         | 99.2       | 5.8         | 4.8         | 6.0         |
| 2         | 5.8         | 6.1         | 7.3         | 6.0         | 2.5         | 93.2       | 6.6         | 5.1         | 4.8         |
| LOCS      | 2           | 7           | 2           | 4           | 2           | 3          | 9           | 6           | 4           |
| REPS      | 3           | 10          | 4           | 4           | 4           | 6          | 9           | 9           | 6           |
| DIFF      | 0.3         | 0.8         | 0.0         | 1.8         | 2.0         | 6.0        | 0.8         | 0.3         | 1.3         |
| PR > T    | .795        | .062*       | .999        | .069*       | .000#       | .020+      | .111        | .562        | .030+       |

|           | ECB 1LF ABS | ECB 2SC ABS | HSK CVR ABS | HSK CVR % MN | OIL T ABS | PRO T ABS | STR T ABS |
|-----------|-------------|-------------|-------------|--------------|-----------|-----------|-----------|
| TOTAL SUM |             |             |             |              |           |           |           |
| 1         | 5.1         | 7.4         | 6.4         | 131          | 4.3       | 10.3      | 71.0      |
| 2         | 6.9         | 7.3         | 5.9         | 120          | 3.9       | 8.6       | 72.5      |
| LOCS      | 4           | 9           | 28          | 28           | 2         | 2         | 2         |
| REPS      | 6           | 10          | 28          | 28           | 2         | 2         | 2         |
| DIFF      | 1.8         | 0.1         | 0.4         | 11           | 0.4       | 1.7       | 1.6       |
| PR > T    | .027+       | .824        | .123        | .096*        | .105      | .095+     | .347      |

*10% SIG
+5% SIG
1% SIG

TABLE 2D

HYBRID COMPARISON REPORT
VARIETY #1 = 38A24
VARIETY #2 = 3752

|  | PRM ABS | PRM SHD ABS | BU ACR ABS | BU ACR % MN | MST % MN | TST WT ABS | EGR WTH % MN | EST CNT % MN | GDU SHD % MN |
|---|---|---|---|---|---|---|---|---|---|
| TOTAL SUM | | | | | | | | | |
| 1 | 96 | 100 | 185.7 | 106 | 100 | 55.9 | 104 | 102 | 102 |
| 2 | 98 | 97 | 172.6 | 99 | 107 | 55.3 | 83 | 97 | 99 |
| LOCS | 4 | 3 | 156 | 156 | 157 | 66 | 64 | 20 | 54 |
| REPS | 4 | 3 | 159 | 159 | 159 | 68 | 64 | 20 | 62 |
| DIFF | 3 | 3 | 13.1 | 7 | 7 | 0.6 | 21 | 5 | 3 |
| PR > T | .000# | .054* | .000# | .000# | .000# | .009# | .000# | .137 | .000# |

|  | GDU SLK % MN | STK CNT % MN | PLT HT % MN | EAR HT % MN | RT LDG % MN | STA GRN % MN | STK LDG % MN | BRT STK % MN | DRP EAR % MN |
|---|---|---|---|---|---|---|---|---|---|
| TOTAL SUM | | | | | | | | | |
| 1 | 101 | 101 | 99 | 97 | 103 | 120 | 103 | 101 | 100 |
| 2 | 99 | 99 | 96 | 91 | 105 | 102 | 99 | 102 | 100 |
| LOCS | 40 | 219 | 66 | 65 | 41 | 74 | 90 | 28 | 17 |
| REPS | 44 | 272 | 71 | 69 | 42 | 76 | 90 | 28 | 17 |
| DIFF | 2 | 1 | 3 | 6 | 2 | 18 | 4 | 1 | 1 |
| PR > T | .000# | .007# | .000# | .000# | .832 | .006# | .001# | .138 | .143 |

|  | GLF SPT ABS | NLF BLT ABS | GOS WLT ABS | STW WLT ABS | ANT ROT ABS | HD SMT ABS | FUS ERS ABS | GIB ERS ABS | EYE SPT ABS |
|---|---|---|---|---|---|---|---|---|---|
| TOTAL SUM | | | | | | | | | |
| 1 | 5.5 | 7.3 | 7.3 | 7.8 | 5.8 | 99.2 | 5.8 | 4.4 | 6.0 |
| 2 | 4.3 | 6.4 | 6.8 | 4.8 | 4.8 | 93.4 | 6.1 | 6.4 | 5.0 |
| LOCS | 2 | 6 | 2 | 4 | 2 | 3 | 9 | 7 | 4 |
| REPS | 3 | 9 | 4 | 4 | 3 | 6 | 9 | 10 | 6 |
| DIFF | 1.3 | 0.8 | 0.5 | 3.0 | 1.0 | 5.8 | 0.3 | 1.9 | 1.0 |
| PR > T | .344 | .175 | .500 | .035+ | .000# | .125 | .438 | .029+ | .066* |

|  | ECB 1LF ABS | ECB 2SC ABS | HSK CVR ABS | HSK CVR % MN | OIL T ABS | PRO T ABS | STR T ABS |
|---|---|---|---|---|---|---|---|
| TOTAL SUM | | | | | | | |
| 1 | 4.5 | 7.4 | 6.3 | 127 | 4.3 | 10.3 | 71.0 |
| 2 | 4.0 | 6.9 | 5.4 | 104 | 4.4 | 9.4 | 70.1 |
| LOCS | 2 | 8 | 34 | 34 | 2 | 2 | 2 |
| REPS | 2 | 8 | 34 | 34 | 2 | 2 | 2 |
| DIFF | 0.5 | 0.5 | 1.0 | 23 | 0.2 | 0.8 | 0.9 |
| PR > T | .500 | .275 | .021+ | .025+ | .205 | .354 | .454 |

*10% SIG
+5% SIG
1% SIG

TABLE 2E

HYBRID COMPARISON REPORT
VARIETY #1 = 38A24
VARIETY #2 = 38N40

|  | PRM ABS | PRM SHD ABS | BU ACR ABS | BU ACR % MN | MST % MN | TST WT ABS | EGR WTH % MN | EST CNT % MN | GDU SHD % MN |
|---|---|---|---|---|---|---|---|---|---|
| TOTAL SUM | | | | | | | | | |
| 1 | 96 | 100 | 187.4 | 106 | 101 | 56.5 | 102 | 106 | 102 |
| 2 | 96 | 101 | 178.1 | 101 | 99 | 55.3 | 84 | 105 | 103 |
| LOCS | 2 | 2 | 138 | 138 | 139 | 57 | 55 | 6 | 50 |

TABLE 2E-continued

HYBRID COMPARISON REPORT
VARIETY #1 = 38A24
VARIETY #2 = 38N40

| | | | | | | | | | |
|---|---|---|---|---|---|---|---|---|---|
| REPS | 2 | 2 | 139 | 139 | 140 | 58 | 55 | 6 | 59 |
| DIFF | 1 | 1 | 9.2 | 5 | 2 | 1.2 | 18 | 2 | 1 |
| PR > T | .072* | .372 | .000# | .000# | .003# | .000# | .000# | .801 | .004# |

| | GDU SLK % MN | STK CNT % MN | PLT HT % MN | EAR HT % MN | RT LDG % MN | STA GRN % MN | STK LDG % MN | BRT STK % MN | DRP EAR % MN |
|---|---|---|---|---|---|---|---|---|---|
| TOTAL SUM | | | | | | | | | |
| 1 | 101 | 100 | 99 | 97 | 104 | 122 | 104 | 101 | 100 |
| 2 | 104 | 101 | 100 | 100 | 106 | 100 | 99 | 102 | 100 |
| LOCS | 40 | 201 | 60 | 59 | 35 | 63 | 78 | 23 | 10 |
| REPS | 45 | 259 | 66 | 64 | 36 | 65 | 78 | 23 | 10 |
| DIFF | 2 | 1 | 1 | 3 | 2 | 22 | 5 | 1 | 0 |
| PR > T | .000# | .039+ | .081* | .035+ | .713 | .002# | .000# | .012+ | .999 |

| | GLF SPT ABS | NLF BLT ABS | GOS WLT ABS | STW WLT ABS | ANT ROT ABS | HD SMT ABS | FUS ERS ABS | GIB ERS ABS | EYE SPT ABS |
|---|---|---|---|---|---|---|---|---|---|
| TOTAL SUM | | | | | | | | | |
| 1 | 5.5 | 7.1 | 7.3 | 7.8 | 4.5 | 99.2 | 5.8 | 4.8 | 6.0 |
| 2 | 6.3 | 6.5 | 7.0 | 5.3 | 3.5 | 98.8 | 5.9 | 4.8 | 6.0 |
| LOCS | 2 | 5 | 2 | 4 | 2 | 3 | 9 | 6 | 4 |
| REPS | 3 | 8 | 4 | 4 | 4 | 6 | 9 | 9 | 6 |
| DIFF | 0.8 | 0.6 | 0.3 | 2.5 | 1.0 | 0.4 | 0.1 | 0.0 | 0.0 |
| PR > T | .205 | .208 | .500 | .030+ | .626 | .740 | .813 | .999 | .999 |

| | | ECB 1LF ABS | ECB 2SC ABS | HSK CVR ABS | HSK CVR % MN | OIL T ABS | PRO T ABS | STR T ABS |
|---|---|---|---|---|---|---|---|---|
| | TOTAL SUM | | | | | | | |
| | 1 | 5.1 | 7.4 | 6.4 | 131 | 4.3 | 10.3 | 71.0 |
| | 2 | 5.3 | 7.5 | 5.1 | 105 | 4.4 | 10.6 | 70.0 |
| | LOCS | 4 | 9 | 28 | 28 | 2 | 2 | 2 |
| | REPS | 6 | 10 | 26 | 28 | 2 | 2 | 2 |
| | DIFF | 0.1 | 0.1 | 1.2 | 27 | 0.2 | 0.3 | 1.0 |
| | PR > T | .718 | .824 | .000# | .000# | .035+ | .402 | .137 |

*10% SIG
+5% SIG
1% SIG

Strip Test Data for Hybrid 38A24

Comparison data was collected from strip tests that were grown by farmers. Each hybrid was grown in strips of 4, 6, 8, 12, etc. rows in fields depending on the siz of the planter used. The data was collected from strip tests that had the hybrids in the same area and weighed. The moisture percentage was determined and bushels per acre was adjusted to 15.5 percent moisture. The number of comparisons represent the number of locations or replications for the two hybrids that were grown in the same field in close proximity and compared.

Comparison strip testing was done between Pioneer Brand Hybrid 38A24 and Pioneer Brand Hybrids 37H24, 37M81, 3752, 3753, 38N40, 38P05, and 38T27. The comparisons come from all the hybrid's adapted growing areas in the United States.

These results are presented in Table 3. As can be seen from the table hybrid 38A24 demonstrates a yield and income advantage over hybrids 37H24, 37M81, 3752, 38N40, and 38P05. The yield advantage ranged from 0.7 bushels per acre to 6.9 bushels per acre. The income advantage over these hybrids ranged $1.57 to $12.06 per acre. Hybrid 38A24 also demonstrated a stalk lodging and root lodging resistance advantage over hybrid 38T27 and was similar in stalk lodging and root lodging resistance to hybrid 3753. Hybrid 38A24's yield advantage plus its advantage for other characteristics over these hybrids will make it an important addition for most of the areas where these hybrids are grown.

TABLE 3

1999 PERFORMANCE CONPARISON REPORT FOR CORN
1 YEAR SUMMARY OF ALL STANDARD TEST TYPES

| Brand | Product | Yield | Moist | Income/Acre | Pop K/Acre | Stand (%) | Roots (%) | Test Wt |
|---|---|---|---|---|---|---|---|---|
| Pioneer | 38A24 | 171.9 | 18.7 | 329.78 | 27.6 | 92 | 96 | 57.8 |
| Pioneer | 37H24 | 171.2 | 18.8 | 328.21 | 28.5 | 91 | 96 | 57.9 |
| Advantage | | .7 | .1 | 1.57 | −.9 | 1 | 0 | −.1 |
| Number of Comparisons | | 159 | 159 | 159 | 145 | 96 | 74 | 156 |
| Percent Wins | | 53 | 57 | 54 | 23 | 38 | 16 | 29 |
| Probability of Difference | | 70 | 73 | 76 | 99 | 13 | 15 | 75 |
| Pioneer | 38A24 | 171.1 | 18.7 | 328.19 | 27.4 | 93 | 96 | 57.7 |
| Pioneer | 37M81 | 165.7 | 18.5 | 318.16 | 28.2 | 94 | 96 | 55.6 |
| Advantage | | 5.4 | −.2 | 10.03 | −.8 | −1 | 0 | 2.1 |
| Number of Comparisons | | 160 | 160 | 160 | 145 | 95 | 73 | 157 |
| Percent Wins | | 76 | 40 | 74 | 24 | 32 | 22 | 93 |
| Probability of Difference | | 99 | 92 | 99 | 99 | 84 | 68 | 99 |
| Pioneer | 38A24 | 152.5 | 16.3 | 297.20 | 2E.8 | 99 | 100 | 58.5 |
| Pioneer | 3752 | 150.8 | 16.8 | 293.92 | 27.2 | 100 | 100 | 58.4 |
| Advantage | | 1.7 | .5 | 3.28 | −.4 | −1 | 0 | |
| Number of Comparisons | | 6 | 6 | 6 | 5 | 3 | 2 | 5 |
| Percent Wins | | 33 | 83 | 33 | 40 | 0 | 0 | 20 |
| Probability of Difference | | 20 | 86 | 23 | 38 | — | — | 63 |
| Pioneer | 38A24 | 211.4 | 19.3 | 404.46 | 30.0 | 100 | 100 | 57.5 |
| Pioneer | 3753 | 216.4 | 19.0 | 415.72 | 30.0 | 100 | 100 | 57.5 |
| Advantage | | −5.0 | −.3 | −11.26 | .0 | 0 | 0 | .0 |
| Number of Comparisons | | 2 | 2 | 2 | 2 | 1 | 1 | 2 |
| Percent Wins | | 50 | 50 | 50 | 0 | 0 | 0 | 50 |
| Probability of Difference | | — | — | — | — | — | — | — |
| Pioneer | 38A24 | 172.6 | 18.8 | 331.16 | 27.7 | 92 | 96 | 57.7 |
| Pioneer | 38N40 | 165.7 | 18.4 | 319.10 | 28.4 | 88 | 96 | 56.1 |
| Advantage | | 6.9 | −.4 | 12.06 | −.7 | 4 | 0 | 1.6 |
| Number of Comparisons | | 159 | 159 | 159 | 144 | 94 | 72 | 156 |
| Percent Wins | | 77 | 39 | 76 | 28 | 47 | 11 | 93 |
| Probability of Difference | | 99 | 99 | 99 | 69 | 25 | 93 | 99 |
| Pioneer | 38A24 | 171.2 | 18.7 | 328.24 | 27.5 | 93 | 96 | 57.7 |
| Pioneer | 38P05 | 167.2 | 17.6 | 324.18 | 28.6 | 89 | 97 | 57.7 |
| Advantage | | 4.0 | −1.1 | 4.06 | −1.1 | 4 | −1 | |
| Number of Comparisons | | 156 | 156 | 156 | 141 | 92 | 73 | 153 |
| Percent Wins | | 69 | 10 | 62 | 17 | 46 | 11 | 38 |
| Probability of Difference | | 99 | 99 | 99 | 99 | 38 | 82 | 44 |
| Pioneer | 38A24 | 172.1 | 18.7 | 330.10 | 27.5 | 92 | 96 | 57.7 |
| Pioneer | 38T27 | 174.2 | 18.7 | 334.30 | 28.3 | 91 | 95 | 57.3 |
| Advantage | | −2.1 | .0 | −4.20 | −.8 | 1 | 1 | .4 |
| Number of Comparisons | | 159 | 159 | 159 | 144 | 96 | 74 | 156 |
| Percent Wins | | 40 | 40 | 38 | 19 | 42 | 20 | 60 |
| Probability of Difference | | 99 | 69 | 99 | 99 | 63 | 45 | 99 |
| Pioneer | 38A24 | 171.7 | 18.7 | 329.44 | 27.5 | 93 | 96 | 57.7 |
| Weighted Avg | | 168.8 | 18.4 | 324.78 | 28.4 | 91 | 96 | 56.9 |
| Advantage | | 2.9 | −.3 | 4.66 | −.9 | 2 | 0 | .8 |
| Number of Comparisons | | 801 | 801 | 801 | 726 | 477 | 369 | 785 |
| Percent Wins | | 63 | 38 | 61 | 22 | 40 | 16 | 62 |
| Probability of Difference | | 99 | 99 | 99 | 99 | 38 | 82 | 99 |

NOTE: The probability values are useful in analyzing if there is a "real" difference in the genetic potential of the products involved. High values are desirable, with 95% considered significant for real differences.

Comparison of Key Characteristics for Hybrid 38A24

Characteristics of Pioneer Hybrid 38A24 are compared to Pioneer Hybrids 38P05, 37M81, 37H24, 3753, 3752, and 38N40 in Table 4. The values given for most traits are on a 1–9 basis. In these cases 9 would be outstanding, while 1 would be poor for the given characteristics. Table 4 shows that hybrid 38A24 has exceptional yield and Head Smut tolerance. The table also indicates that 38A24 also exhibits above average early growth, good tolerance to Stewart's Wilt, Goss's Wilt, and Northern Leaf Blight, as well as good husk cover and drought tolerance. Hybrid 38A24's excellent yield combined with its other favorable agronomic characteristics, including early growth, stand establishment and rapid seed fill make it an important hybrid to its area of adaptation.

TABLE 4

Hybrid Patent Comparisons-Characteristics
Pioneer Hybrid 38A24 vs.Pioneer Hybrids 38P05, 37M81, 37H24, 3753, and 3752

| VARIETY | CRM | SILK CRM | PHY CRM | GDU SILK | GDU PHY | YLD | H/POP | L/POP | D/D | S/S | R/S |
|---|---|---|---|---|---|---|---|---|---|---|---|
| 38A24 | 96 | 97 | 98 | 1210 | 2350 | 9 |   |   | 6 | 5 | 5 |
| 38P05 | 93 | 94 | 94 | 1180 | 2240 | 9 | 9 | 8 | 6 | 5 | 5 |
| 37M81 | 97 | 97 | 97 | 1210 | 2320 | 9 | 9 | 8 | 7 | 4 | 4 |
| 37H24 | 97 | 94 | 96 | 1180 | 2300 | 9 | 9 | 8 | 6 | 4 | 5 |
| 3753 | 96 | 99 | 98 | 1240 | 2350 | 8 | 7 | 8 | 6 | 4 | 5 |
| 3752 | 97 | 96 | 97 | 1200 | 2320 | 7 | 6 | 7 | 7 | 3 | 4 |

| VARIETY | STA GRN | D/T | TST WT | E/G | PLT HT | EAR HT | EAR RET | BRT STK | HSK CVR | GLF SPT | NLF BLT |
|---|---|---|---|---|---|---|---|---|---|---|---|
| 38A24 | 6 | 7 | 6 | 6 | 5 | 5 | 5 |   | 7 | 3 | 7 |
| 38P05 | 6 | 7 | 6 | 5 | 5 | 5 | 5 | 6 | 6 | 3 | 6 |
| 37M81 | 6 | 7 | 4 | 5 | 6 | 7 | 5 | 4 | 6 | 4 | 5 |
| 37H24 | 7 | 6 | 7 | 5 | 5 | 4 | 6 | 6 | 7 | 3 | 5 |
| 3753 | 3 | 6 | 6 | 7 | 6 | 5 | 6 | 2 | 7 | 2 | 7 |
| 3752 | 5 | 7 | 6 | 4 | 4 | 3 | 4 | 7 | 6 | 4 | 6 |

| VARIETY | GOS WLT | STW WLT | ANT ROT | HD SMT | CLN | FUS ERS | GIB ERS | EYE SPT | COM RST | ECB 1ST | ECB 2ND |
|---|---|---|---|---|---|---|---|---|---|---|---|
| 38A24 | 7 | 7 |   | 9 |   | 3 | 4 | 6 |   | 4 |   |
| 38P05 | 7 | 7 | 3 | 8 |   | 5 | 5 | 5 | 5 | 4 | 5 |
| 37M81 | 6 | 4 | 5 | 8 |   |   | 5 | 5 | 7 | 3 | 3 |
| 37H24 | 8 | 5 | 3 | 8 |   | 5 | 4 | 5 | 6 | 5 | 4 |
| 3753 | 6 |   | 2 | 7 |   | 6 | 4 | 6 | 7 | 6 | 5 |
| 3752 | 7 | 3 | 4 | 8 | 5 | 4 | 6 | 5 | 4 | 5 | 3 |

Silage Data Comparison for Pioneer Hybrid 38A24

Table 5A through 5E compare of silage characteristics of Pioneer Brand Hybrid 38A24 against Pioneer Brand Hybrids 3752, 37H24, 37M81, 38N40, and 38P05, respectively. The results indicate that hybrid 38A24 demonstrates superior silage yield to all of the hybrids. Hybrid 38A24 also shows more dry matter content than hybrids 37H24, 37M81, and 38N40; more starch content than hybrids 3752 and 37H24; a higher percentage of acid detergent fiber than hybrids 3752, 37M81, and 38N40; and a higher percentage of crude protein than hybrid 37M81. Hybrid 38A24's strong silage characteristics will make it an important silage hybrid for its area of adaptation.

TABLE 5A

HYBRID SILAGE COMPARISON REPORT
VARIETY #1 - 38A24
VARIETY #2 - 3752

|  | VARIETY | YIELD | DM | STARCH | ADF | CP |
|---|---|---|---|---|---|---|
| Total Sum | 1 | 24.53 | 39.8 | 31.9 | 21.9 | 7.4 |
|  | 2 | 23.35 | 39.9 | 31.8 | 21.5 | 7.4 |

TABLE 5B

HYBRID SILAGE COMPARISON REPORT
VARIETY #1 - 38A24
VARIETY #2 - 37H24

|  | VARIETY | YIELD | DM | STARCH | ADF | CP |
|---|---|---|---|---|---|---|
| Total Sum | 1 | 26.02 | 39.2 | 34.0 | 20.4 | 7.3 |
|  | 2 | 25.82 | 38.0 | 33.2 | 21.1 | 7.5 |

TABLE 5C

HYBRID SILAGE COMPARISON REPORT
VARIETY #1 - 38A24
VARIETY #2 - 37M81

|  | VARIETY | YIELD | DM | STARCH | ADF | CP |
|---|---|---|---|---|---|---|
| Total Sum | 1 | 26.25 | 39.6 | 34.4 | 20.5 | 7.3 |
|  | 2 | 25.71 | 38.6 | 34.7 | 20.3 | 7.2 |

TABLE 5D

HYBRID SILAGE COMPARISON REPORT
VARIETY #1 - 38A24
VARIETY #2 - 38N40

|  | VARIETY | YIELD | DM | STARCH | ADF | CP |
|---|---|---|---|---|---|---|
| Total Sum | 1 | 26.08 | 39.5 | 34.8 | 20.1 | 7.3 |
|  | 2 | 25.30 | 38.8 | 36.5 | 19.1 | 7.4 |

TABLE 5E

HYBRID SILAGE COMPARISON REPORT
VARIETY #1 - 38A24
VARIETY #2 - 38P05

|  | VARIETY | YIELD | DM | STARCH | ADF | CP |
|---|---|---|---|---|---|---|
| Total Sum | 1 | 26.02 | 39.2 | 34.0 | 20.4 | 7.3 |
|  | 2 | 25.47 | 40.7 | 34.1 | 21.3 | 7.4 |

Further Embodiments of the Invention

This invention includes hybrid maize seed of 38A24 and th hybrid maiz plant produced therefrom. The foregoing was set forth by way of example and is not intended to limit the scope of the invention.

As used herein, the term plant includes plant cells, plant protoplasts, plant cell tissue cultures from which maize plants can be regenerated, plant calli, plant clumps, and plant cells that are intact in plants, or parts of plants, such as embryos, pollen, ovules, flowers, kernels, ears, cobs, leaves, seeds, husks, stalks, roots, root tips, anthers, silk and the like.

Duncan, Williams, Zehr, and Widholm, *Planta*, (1985) 165:322–332 reflects that 97% of the plants cultured which produced callus were capable of plant regeneration. Subsequent experiments with both inbreds and hybrids produced 91% regenerable callus which produced plants. In a further study in 1988, Songstad, Duncan & Widholm in Plant Cell Reports (1988), 7:262–265 reports several media additions which enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter*, 60:6465 (1986), refers to somatic embryogenesis from glume callus cultures and B. V. Conger, et al., *Plant Cell Reports*, 6:345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize is described in European Patent Application, publication 160,390, incorporated herein by reference. Maize tissue culture procedures are also described in Green and Rhodes, "Plant Regeneration in Tissue Culture of Maize," *Maize for Biological Research* (Plant Molecular Biology Association, Charlottesville, Va. 1982, at 367–372) and in Duncan, et al., "The Production of Callus Capable of Plant Regeneration from Immature Embryos of Numerous Zea Mays Geneotypes," 165 *Planta* 322–332 (1985). Thus, another aspect of this invention is to provide cells which upon growth and differentiation produce maize plants having the genotype of 38A24.

Transformation of Size

With the advent of molecular biological techniques that have allowed the isolation and characterization of genes that encode specific protein products, scientist in the field of plant biology developed a strong interest in engineering the genome of plants to contain and express foreign genes, or additional, or modified versions of native or endogenous genes (perhaps driven by different promoters) in order to alter the traits of a plant in a specific manner. Such foreign, additional and/or modified genes are referred to herein collectively as "transgenes". Over the last fifteen to twenty years several methods for producing transgenic plants have been developed, and the present invention, in particular embodiments, relates to transgenic versions of the claimed hybrid maize line 38A24.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used, alone or in combination with other plasmids, to provide transformed maize plants, using transformation methods as described below to incorporate transgenes into the genetic material of the maize plant(s).

Expression Vectors for Maize Transformation

Marker Genes

Expression vectors include at least one genetic marker, operably linked to a regulatory element (a promoter, for example) that allows transformed cells containing the marker to be either recovered by negative selection, i.e. inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80: 4803 (1983). Another commonly used selectable marker gene is the hygromycin phosphotransferase gene which confers resistance to the antibiotic hygromycin. Vanden Elzen et al., *Plant Mol. Biol.*, 5: 299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.*, 210: 86 (1987), Svab et al., *Plant Mol. Biol.* 14: 197 (1990), Hille et al., *Plant Mol. Biol.* 7: 171 (1986). Other selectable marker genes confer resistance to herbicides such as glyphosate, glufosinate or broxynil. Comai et al., *Nature* 317: 741–744 (1985), Gordon-Kamm et al., *Plant Cell* 2: 603–618 (1990) and Stalker et al., *Science* 242: 419–423 (1988).

Other selectable marker genes for plant transformation are not of bacterial origin. These genes include, for example, mouse dihydrofolate reductase, plant 5 -enolpyruvylshikimate-3 -phosphate synthase and plant acetolactate synthase. Eichholtz et at, *Somatic Cell Mol. Genet.* 13: 67 (1987), Shah et al., *Science* 233: 478 (1986), Charest et al, *Plant Cell Rep.* 8: 643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5: 387 (1987)., Teeri et al., *EMBO J.* 8: 343 (1989), Koncz et al., *Proc. Natl. Acad. Sci. U.S.A.* 84:131 (1987), De Block et al., *EMBO J.* 3: 1681 (1984). Another approach to the identification of relatively rare transformation events has been use of a gene that encodes a dominant constitutive regulator of the *Zea mays* anthocyanin pigmentation pathway. Ludwig et al., *Science* 247: 449 (1990).

Recently, in vivo methods for visualizing GUS activity that do not require destruction of plant tissue have been made available. Molecular Probes Publication 2908, Imagene Green™, p. 14 (1993) and Naleway et at., *J. Cell Biol.*

115: 15Ia (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein "promoter" includes reference to a region of DNA upstream from the start of transcription and involved in recognition and binding of RNA polym rase and other proteins to initiate transcription. A "plant promoter" is a promoter capable of initiating transcription in plant cells. Examples of promoters under dev lopmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constituitive" promoters. A "constitutive" promoter is a promoter which is active under most environmental conditions.

A. Inducible Promoters

An inducible promoter is operably linked to a gene for expression in maize. Optionally, the inducible promoter is operably linked to a nucleotide sequence encoding a signal sequence which is operably linked to a gene for expression in maize. With an inducible promoter the rate of transcription increases in response to an inducing agent.

Any inducible promoter can be used in the instant invention. See Ward et al. *Plant Mol. Biol.* 22: 361–366 (1993). Exemplary inducible promoters include, but are not limited to, that from the ACEI system which responds to copper (Mett et al. *PNAS* 90: 4567–4571 (1993)); In2 gene from maize which responds to benzenesulfonamide herbicide safeners (Hershey et al., *Mol. Gen. Genetics* 227: 229–237 (1991) and Gatz et al., *Mol. Gen. Genetics* 243: 32–38 (1994)) or Tet repressor from Tn10 (Gatz et at., *Mol. Gen. Genet.* 227: 229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88: 0421 (1991).

B. Constitutive Promoters

A constitutive promoter is operably linked to a gene for expression in maize or the constitutive promoter is operably linked to a nucleotide sequence encoding a signal sequence which is operably linked to a gene for expression in maize.

Many different constitutive promoters can be utilized in the instant invention. Exemplary constitutive promoters include, but are not limited to, the promoters from plant viruses such as the 35S promoter from CaMV (Odell et al., *Nature* 313: 810–812 (1985) and the promoters from such genes as rice actin (McElroy et al., *Plant Cell* 2: 163–171 (1990)); ubiquitin (Christensen et al., *Plant Mol. Biol.* 12: 619–632 (1989) and Christensen et al, *Plant Mol. Biol.* 18: 675689 (1992)): pEMU (Last et al., *Theor. Appl. Genet.* 81: 581–588 (1991)); MAS (Velten et al., *EMBO J.* 3: 2723–2730 (1984)) and maize H3 histone (Lepetit et al., *Mol. Gen. Genet.* 231: 276–285 (1992) and Atanassova et al., *Plant Journal* 2 (3): 291–300 (1992)).

The ALS promoter, a Xbal/Ncol fragment 5' to the *Brassica napus* ALS3 structural gene (or a nucleotide sequence that has substantial sequence similarity to said Xbal/Ncol fragment), represents a particularly useful constitutive promoter. See PCT application WO96/30530.

C. Tissue-specific or Tissue-preferred Promoters

A tissue-specific promoter is operably linked to a gene for expression in maize. Optionally, the tissue-specific promoter is operably linked to a nucleotide sequence encoding a signal sequence which is operably linked to a gene for expression in maize. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter,-such as that from the phaseolin gene (Murai et al., *Science* 23: 476482 (1983) and SenguptaGopalan et al., *Proc. Natl. Acad. Sci. USA* 82: 3320–3324 (1985)); a leaf-specific and light-induced promoter such as that from cab or rubisco (Simpson et al., *EMBO J.* 4(11): 2723–2729 (1985) and Timko et al., *Nature* 318: 579–582 (1985)); an anther-specific promoter such as that from LAT52 (Twell et al., *Mol. Gen. Genet.* 217: 240245 (1989)); a pollen-specific promoter such as that from Zm13 (Guerrero et al., *Mol. Gen. Genet.* 224: 161–168 (1993)) or a microspore-preferred promoter such as that from apg (Twell et al., *Sex. Plant Reprod.* 6: 217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art. See, for example, Becker et al., *Plant Mol. Biol.* 20: 49 (1992), Close, P. S., Master's Thesis, Iowa State University (1993), Knox, C., et al., "Structure and Organization of Two Divergent Alpha-Amylase Genes From Barley", *Plant Mol. Biol.* 9: 3–17 (1987), Lemer et al., *Plant Physiol.* 91: 124–129 (1989), Fontes et al., *Plant Cell* 3: 483496 (1991), Matsuoka et al., *Proc. Natl. Acad. Sci.* 88: 834 (1991), Gould et al., *J. Cell Biol* 108: 1657 (1989), Creissen et al., *Plant J.* 2: 129 (1991), Kalderon, D., Robers, B., Richardson, W., and Smith A., "A short amino acid sequence able to specify nuclear location", *Cell* 39: 499–509 (1984), Stiefel, V., Ruiz-Avila, L., Raz R., Valles M., Gomez J., Pages M., Martinez-Izquierdo J., Ludevid M., Landale J., Nelson T., and Puigdomenech P., "Expression of a maize cell wall hydroxyproline-rich glycoprotein gene in early leaf and root vascular differentiation", *Plant Cell* 2: 785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92–6 (1981).

According to a preferred embodiment, the transgenic plant provided for commercial production of foreign protein is maize. In another preferred embodiment, the biomass of interest is seed. For the relatively small number of transgenic plants that show higher levels of expression, a genetic map can be generated, primarily via conventional Restriction Fragment Length Polymorphisms (RFLP), Polymerase Chain Reaction (PCR) analysis, and Simple Sequence Repeats (SSR) which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269–284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below.

1. Genes that Confer Resistance to Pests or Disease And That Encode:

(A) Plant disease resistance genes. Plant defens s are often activated by specific interaction between th product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266: 789 (1994) (cloning of the tomato Cf-9 gene for resistance to *Cladosporium fulvum*); Martin et al., *Science* 262: 1432 (1993) (tomato Pto gene for resistance to *Pseudomonas synngae* pv. tomato encodes a protein kinase); Mindrinos et al., *Cell* 78: 1089 (1994) (Arabidopsis RSP2 gene for resistance to *Pseudomonas sydngae*).

(B) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt δ-endotoxin gene. Moreover, DNA molecules encoding δ-endotoxin genes can be purchased from American Type Culture Collection (Rockville, Md.), for example, under ATCC Accession Nos. 40098, 67136, 31995 and 31998.

(C) A lectin. See, for example, the disclosure by Van Damme et al., *Plant Molec. Biol.* 24: 25 (1994), who disclose the nucleotide sequences of several *Clivia miniata* mannose-binding lectin genes.

(D) A vitamin-binding protein, such as avidin. See PCT application US93/06487 the contents of which are hereby incorporated by. The application teaches the use of avidin and avidin homologues as larvicides against insect pests.

(E) An enzyme inhibitor, for example, a protease inhibitor or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of cDNA encoding tobacco proteinase inhibitor I), and Sumitani et al., *Biosci. Biotech. Biochem.* 57: 1243 (1993) (nucleotide sequence of *Streptomyces nitrosporeus* α-amylase inhibitor).

(F) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(G) An insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific, paralytic neurotoxins.

(H) An insect-specific venom produced in nature by a snake, a wasp, etc. For example, see Pang et al., *Gene* 116: 165 (1992), for disclosure of heterologous expression in plants of a gene coding for a scorpion insectotoxic peptide.

(I) An enzyme responsible for an hyperaccumulation of a monterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene.

(K) A molecule that stimulates signal transduction. For example, see the disclosure by Botella et al, *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(L) A hydrophobic moment peptide. See PCT application WO95/16776 (disclosure of peptide derivatives of Tachyplesin which inhibit fungal plant pathogens) and PCT application WO095118855 (teaches synthetic antimicrobial peptides that confer disease resistance), the respective contents of which are hereby incorporated by reference.

(M) A membrane permease, a channel former or a channel blocker. For example, see the disclosure by Jaynes et al., *Plant Sci.* 89: 43 (1993), of heterologous expression of a cecropin-β lytic peptide analog to render transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or dis ase development ffected by the virus from which the coat protein gene is derived, as well as by related viruses. See Beachy at al., *Ann. Rev. Phytopathol.* 28: 451 (1990). Coatprotein-mediated resistance has been conferred upon transform d plants against alfalfa mosaic virus, cucumber mosaic virus, tobacco streak virus, potato virus X, potato virus Y, tobacco etch virus, tobacco rattle virus and tobacco mosaic virus. Id.

(O) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(P) A virus-specific antibody. See, for example, Taviadoraki et al., *Nature* 366: 469 (1993), who show that transgenic plants expressing recombinant antibody genes are protected from virus attack.

(Q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-Dgalacturonase. See Lamb et al., *Bio/Technology* 10: 1436 (1992). The doning and characterization of a gene which encodes a bean endopolygalacturonase-inhibiting protein is described by Toubart et al., *Plant J.* 2: 367 (1992).

(R) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

2. Genes that Confer Resistance to a Herbicide, for Example:

(A) A herbicide that inhibits the growing point or meristem, such as an imidazalinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah et al., which discloses the nucleotide sequence of a form of EPSP which can confer glyphosat resistance. A DNA molecule encoding a mutant aroA gene can b obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which conf r resistance to herbicides such as L-phosphinothricin. The nucleotide sequence of a phosphinothricin-acetyltransferase gene is provided in European application No. 0 242 246 to Leemans et al. De Greef et al., *Bio/Technology* 7: 61 (1989), describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+ genes) and a benzonitrile (nitrilase gene). Przibilla et al., *Plant Cell* 3: 169 (1991), describe the transformation of Chiamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

3. Genes that Confer or Contribute to a Value-added Trait, Such As:

(A) Modified fatty acid metabolism, for example, by transforming a plant with an antisense gene of stearoyl-ACP desaturase to increase stearic acid content of the plant. See Knultzon et al., *Proc. Natl. Acad. Sci. USA* 89: 2624 (1992).

(B) Decreased Phytate Content
  (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.
  (2) A gene could be introduced that reduces phytate content. In maize, this, for example, could be accomplished, by cloning and then reintroducing DNA associated with the single allele which is responsible for maize mutants characterized by low levels of phytic acid. See Raboy et al, *Maydica* 35: 383 (1990).

(C) Modified carbohydrate composition effected, for example, by transforming plants with a gene coding for an enzyme that alters the branching pattern of starch. See Shiroza et al., *J. Bacteriol.* 170: 810 (1988) (nucleotide sequence of *Streptococcus mutans* fructosyltransferase gene), Steinmetz et al., *Mol. Gen. Genet.* 200: 220 (1985) (nucleotide sequence of *Bacillus subtilis* I vansucrase gene), Pen et al., *Bio/Technology* 10: 292 (1992) (production of transgenic plants that express *Bacillus licheniformis* α-amylase), Elliot et al., *Plant Molec. Biol.* 21: 515 (1993) (nucleotide sequences of tomato invertase genes), Søgaard et al., *J. Biol. Chem.* 268: 22480 (1993) (site-directed mutagenesis of barley α-amylase gene), and Fisher et al., *Plant Physiol.* 102: 1045 (1993) (maize endosperm starch branching enzyme II).

Methods for Maize Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R.

and Thompson, J. E. Eds. (CRC Press, Inc., Boca Raton, 1993) pages 89–119.

A. Agrobacterium-mediated Transformation

One method for introducing an expression vector into plants is based on the natural transformation system of Agrobacterium. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10: 1 (1991). Descriptions of Agrobacterdum vector systems and methods for Agrobactedum-mediated gene transfer are provided by Gruber et al., supra, Miki et al., supra, and Moloney et al., *Plant Cell Reports* 8: 238 (1989). See also, U.S. Pat. No. 5,591,616, issued Jan. 7, 1997.

B. Direct Gene Transfer

Despite the fact the host range for Agrobacternum-mediated transformation is broad, some major cereal crop species and gymnosperms have generally been recalcitrant to this mode of gene transfer, even though some success has recently been achieved in rice and maize. Hiei et al., *The Plant Journal* 6: 271–282 (1994); U.S. Pat. No. 5,591,616, issued Jan. 7, 1997. Several methods of plant transformation, collectively referred to as direct gene transfer, have been developed as an alternative to Agrobacterum-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accel rates th microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559 563 (1988), Sanford, J. C., *Physiol Plant* 79: 206 (1990), Klein et al., *Biotechnology* 10: 268 (1992). In maize, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et at, *EMBO J.*, 4: 2731 (1985), Christou et at, *Proc. Natl. Acad. Sci. U.S.A.* 84: 3962 (1987). Direct uptake of DNA into protoplasts using CaCl2 precipitation, polyvinyl alcohol or poly-L-ornithine have also been reported. Hain et al., *Mol. Gen. Genet.* 199: 161 (1985) and Draper et al., *Plant Cell Physiol.* 23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4: 1495–1505 (1992) and Spencer et al., *Plant Mol. Biol.* 24: 5161 (1994).

Following transformation of maize target tissues, expression of the above-described selectable marker genes allows for preferential selection of transformed cells, tissues and/or plants, using regeneration and selection methods now well known in the art.

The foregoing methods for transformation would typically be used for producing transgenic inbred lines. Transgenic inbred lines could then be crossed, with another (non-transformed or transformed) inbred line, in order to produce a transgenic hybrid maize plant. Alternatively, a genetic trait which has been engineered into a particular maize line using the foregoing transformation techniques could be moved into another line using traditional backcrossing techniques that are well known in the plant breeding arts. For example, a backcrossing approach could be used to move an engineered trait from a public, nonlite line into an elite line, or from a hybrid maize plant containing a foreign gene in its genome into a line or lines which do not contain that gene. As used herein, "crossing" can refer to a simple X by Y cross, or the process of backcrossing, depending on the context.

Industrial Applicability

Maize is used as human food, livestock feed, and as raw material in industry. The food uses of maize, in addition to human consumption of maize kernels, include both products of dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize are also used in industry. Stalks and husks are made into paper and wallboard and cobs are used for fuel and to make charcoal.

The seed of the hybrid maize plant and various parts of the hybrid maize plant and transgenic versions of the foregoing, can be utilized for human food, livestock feed, and as a raw material in industry.

Although the foregoing invention has been described in some detail by way of illustration and example for purposes of clarity and understanding, it will be obvious that certain changes and modifications such as single gene modifications and mutations, somoclonal variants, variant individuals selected from large populations of the plants of the instant hybrid may be practiced within the scope of the invention, as limited only by the scope of the appended claims.

Deposits

Applicant(s) have made a deposit of at least 2500 seeds of hybrid maize plant 38A24 and inbred parent plants GE533340 with the American Type Culture Collection (ATCC), 10801 University Boulevard, Manassas, Va. 20110-2209 USA, ATCC Deposit Nos. PTA-4265, PTA-4287 and PTA-1282, respectively. The seeds deposited with the ATCC on May 3, 2002, May 6, 2002 and Feb. 3, 2002, respectively were taken from the deposit maintained by Pioneer Hi-Brend International, Inc., 800 Capital Square, 400 Locust Street, Des Moines, Iowa 50309-2340, since prior to the filling date of this application. Access to this deposit will be available during the pendancy of the application to the Commissioner of Patents and Trademarks and persons determined by the Commissioner to be entitled thereto upon request. Upon allowance of any claims in the application, the Applicant(s) will make available to the public, pursuant to 37 C.F.R. § 1.808, sample(s) of the deposit of at least 2500 seeds of hybrid maize plant 38A24 and inbred parent plants GE533340 and GE501400 with the American Type Culture Collection (ATCC), 10801 University Boulevard, Manassas, Va. 20110-2209. This deposit of seeds of hybrid maize plant 38A24 and inbred parent plants GE533340 and GE501400 will be maintained in the ATCC Depository, which is a public depository for a period of 30 years after the most recent request or for the enforceable life of the patent, whichever is longer, and will be replaced if it becomes nonviable during that period. Additionally, Applicant(s) have satisfied all the requirements of 37 C.F.R. § 1.801–1.809, including providing an indication of the viability of the sample upon deposit. Applicant(s) have no authority to waive any restrictions imposed by law on the transfer of biological material or its transportation in commerce. Applicant(s) do not waive any infringement of its rights granted under this patent or under the Plant Variety Protection Act (7 USC 2321 et seq.).

What is claimed is:

1. Seed of hybrid maize variety designated 38A24, representative seed of said variety having been deposited under ATCC Accession number PTA-4265.

2. A maize plant, or a part thereof, produced by growing the seed of claim 1.

3. Pollen of the plant of claim 2.

4. An ovule of the plant of claim 2.

5. A tissue culture of regenerable cells produced from the plant of claim 2.

6. Protoplasts produced from the tissue culture of claim 5.

7. The tissue culture of claim 5, wherein cells of the tissue culture are from a tissue selected from the group consisting of leaf, pollen, embryo, root, root tip, anther, silk, flower, kernel, ear, cob, husk and stalk.

8. A maize plant regenerated from the tissue culture of claim 5, said plant having all the morphological and physiological characteristics of hybrid maize plant 38A24, representative seed of said plant having been deposited under ATCC Accession No. PTA-4265.

9. A method for producing an F1 hybrid maize seed, comprising crossing the plant of claim 2 with a different maize plant and harvesting the resultant F1 hybrid maize seed.

10. A maize plant, or a part thereof, having all the physiological and morphological characteristics of the hybrid maize plant 38A24, representative seed of said plant having been deposited under ATCC Accession No. PTA-4265.

11. A method of introducing a desired trait into a hybrid maize variety 38A24 comprising:
(a) crossing at least one of inbred maize parent plants GE533340 and GE501400, representative seed of which have been deposited under ATCC Accession Nos. as PTA-4287 and PTA-1282 respectively, with another maize line that comprises a desired trait, to produce F1 progeny plants, wherein the desired trait is selected from the group consisting of male sterility, herbicide resistance, insect resistance, disease resistance and waxy starch;
(b) selecting said F1 progeny plants that have the desired trait to produce selected F1 progeny plants;
(c) backcrossing the selected progeny plants with said inbred maize parent plant to produce backcross progeny plants;
(d) selecting for backcross progeny plants that have the desired trait and morphological and physiological characteristics of said inbred maize parent plant to produce selected backcross progeny plants;
(e) repeating steps (c) and (d) three or more times in succession to produce a selected fourth or higher backcross progeny plants; and
(f) crossing said fourth or higher backcross progeny plant with the other inbred maize parent plant to produce a hybrid maize variety 38A24 with the desired trait and all of the morphological and physiological characteristics of hybrid maize variety 38A24 listed in Table 1 as determined at the 5% significance level when grown in the same environmental conditions.

12. A plant produced by the method of claim 11, wherein the plant has the desired trait and all of the physiological and morphological characteristics of hybrid maize variety 38A24 listed in Table 1 as determined at the 5% significance level when grown in the same environmental conditions.

13. The plant of claim 12 wherein the desired trait is herbicide resistance and the resistance is conferred to an herbicide selected from the group consisting of: imidazolinone, sulfonylurea, glyphosate, glufosinate, L-phosphinothricin, triazine and benzonitrile.

14. The plant of claim 12 wherein the desired trait is insect resistance and the insect resistance is conferred by a transgene encoding a *Bacillus thuringiensis* endotoxin.

15. The plant of claim 12 wherein the desired trait is male sterility and the trait is conferred by a cytoplasmic nucleic acid molecule that confers male sterility.

16. A method of modifying fatty acid metabolism, phytic acid metabolism or carbohydrate metabolism in a hybrid maize variety 38A24 comprising:
(a) crossing at least one of inbred maize parent plants GE533340 and GE501400, representative seed of which have been deposited under ATCC Accession Nos. as PTA-4287 and PTA-1282 respectively, with another maize line that comprises a nucleic acid molecule encoding an enzyme selected from the group consisting of phytase, stearyl-ACP desaturase, fructosyltransferase, levansucrase, alpha-amylase, invertase and starch branching enzyme;
(b) selecting said F1 progeny plants that have said nucleic acid molecule to produce selected F1 progeny plants;
(c) backcrossing the selected progeny plants with said inbred maize parent plant to produce backcross progeny plants;
(d) selecting for backcross progeny plants that have said nucleic acid molecule and morphological and physiological characteristics of said inbred maize parent plant to produce selected backcross progeny plants;
(e) repeating steps (c) and (d) three or more times in succession to produce a selected fourth or higher backcross progeny plants; and
(f) crossing said fourth or higher backcross progeny plant with the other inbred maize parent plant to produce a hybrid maize variety 38A24 that comprises said nucleic acid molecule and has all of the morphological and physiological characteristics of hybrid maize variety 38A24 listed in Table 1 as determined at the 5% significance level when grown in the same environmental conditions.

17. A plant produced by the method of claim 16, wherein the plant comprises the nucleic acid molecule and has all of the physiological and morphological characteristics of hybrid maize variety 38A24 listed in Table 1 as determined at the 5% significance level when grown in the same environmental conditions.

18. A method for producing a maize seed, comprising crossing the plant of claim 2 with itself or a different maize plant and harvesting the resultant maize seed.

* * * * *

UNITED STATES PATENT AND TRADEMARK OFFICE
CERTIFICATE OF CORRECTION

PATENT NO.   : 6,777,596 B1
DATED        : August 17, 2004
INVENTOR(S)  : Carrigan, Lori L.

It is certified that error appears in the above-identified patent and that said Letters Patent is hereby corrected as shown below:

Column 38,
Line 53, should read -- GE533340 and GE501400 with the American Type Culture Collection --
Line 57, should read -- the ATCC on May 3, 2002, May 6, 2002 and
February 3, 2000. --
Line 59, should read -- Pioneer Hi-Bred International, Inc., 800 Capital Square, --

Column 39,
Line 4, should read -- sity Boulevard, Manassas, Virginia 20110-2209. This deposit of --
Line 5, should read -- seed of hybrid maize plant 38A24 and inbred parent plants --
Line 7, should read -- Depository, which is a public depository, for a period of 30 --
Line 8, should read -- years, or 5 years after the most recent request, or for the enforceable life --

Signed and Sealed this

Twenty-first Day of December, 2004

JON W. DUDAS
*Director of the United States Patent and Trademark Office*